(12) United States Patent  (10) Patent No.: US 9,277,190 B2
Igarashi et al.  (45) Date of Patent: Mar. 1, 2016

(54) ENDOSCOPE APPARATUS

(71) Applicant: OLYMPUS CORPORATION, Tokyo (JP)

(72) Inventors: Makoto Igarashi, Hachioji (JP); Tetsuo Nonami, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 13/896,881

(22) Filed: May 17, 2013

(65) Prior Publication Data

US 2013/0293693 A1 Nov. 7, 2013

Related U.S. Application Data

(63) Continuation of application No. PCT/JP2012/078743, filed on Nov. 6, 2012.

(30) Foreign Application Priority Data

Mar. 30, 2012 (JP) ................. 2012-082286

(51) Int. Cl.
*H04N 7/18* (2006.01)
*A61B 1/00* (2006.01)
(Continued)

(52) U.S. Cl.
CPC ............ *H04N 7/183* (2013.01); *A61B 1/00009* (2013.01); *A61B 1/0638* (2013.01); *G06T 5/009* (2013.01); *A61B 1/0646* (2013.01); *A61B 1/0684* (2013.01); *A61B 5/489* (2013.01);
(Continued)

(58) Field of Classification Search
CPC ............ G06T 6/00; A61B 5/489; H94N 7/18; H04N 7/18
See application file for complete search history.

(56) References Cited

U.S. PATENT DOCUMENTS

| 4,959,710 A | 9/1990 | Uehara et al. |
| 2003/0176768 A1 | 9/2003 | Gono et al. |

(Continued)

FOREIGN PATENT DOCUMENTS

| EP | 1302152 A1 | 4/2003 |
| EP | 2 604 170 A1 | 6/2013 |

(Continued)

OTHER PUBLICATIONS

Extended Supplementary European Search Report dated Jul. 28, 2015 from related European Application No. 12 87 2387.1.

*Primary Examiner* — Geepy Pe
*Assistant Examiner* — Joseph Becker
(74) *Attorney, Agent, or Firm* — Scully, Scott, Murphy & Presser, PC

(57) ABSTRACT

An endoscope apparatus includes a light source device, an image pickup device, and an observation monitor. The video processor applies, on the basis of a difference between a first image signal having a peak wavelength of a spectral characteristic and a second image signal having a peak wavelength of the spectral characteristic that a value in the absorption characteristic is lower than the value in the absorption characteristic of the first image signal and a scattering characteristic of the living tissue is suppressed more than the scattering characteristic of the first image signal between a wavelength band including a maximum value and a wavelength band at a minimum value in an absorption characteristic of a living tissue, processing for enhancing the first image signal and generates an enhanced and corrected image signal.

13 Claims, 26 Drawing Sheets

(51) Int. Cl.
*A61B 1/06* (2006.01)
*G06T 5/00* (2006.01)
*A61B 5/00* (2006.01)

(52) U.S. Cl.
CPC ............... *G06T 2207/10024* (2013.01); *G06T 2207/10068* (2013.01); *G06T 2207/30101* (2013.01)

(56) References Cited

U.S. PATENT DOCUMENTS

| | | | |
|---|---|---|---|
| 2007/0153542 A1* | 7/2007 | Gono et al. | 362/574 |
| 2009/0075391 A1* | 3/2009 | Fulghum, Jr. | 436/164 |
| 2009/0091614 A1* | 4/2009 | Gono et al. | 348/68 |
| 2009/0289200 A1* | 11/2009 | Ishii | 250/459.1 |
| 2010/0004513 A1* | 1/2010 | MacKinnon et al. | 600/180 |
| 2010/0054576 A1 | 3/2010 | Tsujita | |
| 2011/0237884 A1 | 9/2011 | Saito | |
| 2012/0053434 A1* | 3/2012 | Saito | 600/324 |
| 2012/0154567 A1* | 6/2012 | Yamaguchi et al. | 348/68 |
| 2012/0184812 A1* | 7/2012 | Terakawa | 600/109 |
| 2013/0113904 A1* | 5/2013 | Wang | 348/65 |

FOREIGN PATENT DOCUMENTS

| | | |
|---|---|---|
| EP | 2 687 145 A1 | 1/2014 |
| JP | 01308531 A | 12/1989 |
| JP | 2000041942 | 2/2000 |
| JP | 2002034893 A | 2/2002 |
| JP | 2010-142547 A | 7/2010 |
| WO | WO 0207588 A1 | 1/2002 |

\* cited by examiner

ENDOSCOPE APPARATUS

CROSS REFERENCE TO RELATED APPLICATION

This application is a continuation application of PCT/JP2012/078743 filed on Nov. 6, 2012 and claims benefit of Japanese Application No. 2012-082286 filed in Japan on Mar. 30, 2012, the entire contents of which are incorporated herein by this reference.

BACKGROUND OF THE INVENTION

1. Field of the Invention

The present invention relates to an endoscope apparatus and, more particularly, to an endoscope apparatus capable of displaying a blood vessel on an inside of a subject.

2. Description of the Related Art

Conventionally, in a medical field, minimally invasive various kinds of tests and operations have been performed using an endoscope. A surgeon can insert the endoscope into a body cavity, observe an image of an object picked up by an image pickup apparatus provided at a distal end portion of an endoscope insertion portion, and, according to necessity, apply treatment to a lesion site using a treatment instrument inserted through a treatment instrument channel. An operation performed using the endoscope has an advantage that a physical burden on a patient is small because laparotomy and the like are not performed.

An endoscope apparatus includes an endoscope, an image processing device connected to the endoscope, and an observation monitor. An image of a lesion site is picked up by an image pickup device provided at a distal end portion of an endoscope insertion portion. The image is displayed on the monitor. A surgeon can perform a diagnosis or necessary treatment while looking at the image displayed on the monitor.

With some endoscope apparatus, not only normal light observation performed using white light but also special light observation performed using special light such as infrared light can be performed in order to observe a blood vessel on an inside.

In the case of an infrared endoscope apparatus, for example, indocyanine green (ICG) having a characteristic of an absorption peak in near infrared ray near a wavelength of 805 nm is injected into blood of a patient as a drug. Infrared light near a wavelength of 805 nm and near 930 nm is irradiated on an object in time division manner from a light source device. A signal of an object image picked up by a CCD is inputted to a processor of the infrared endoscope apparatus. For example, as disclosed in Japanese Patent Application Laid-Open Publication No. 2000-41942, concerning such an infrared endoscope apparatus, as a processor, a device that allocates an image near a wavelength of 805 nm to a green signal (G), allocates an image near a wavelength of 930 nm to a blue signal (B), and outputs the signals to a monitor is proposed. Since the image of the infrared light near 805 nm often absorbed by the ICG is allocated to green, a surgeon can observe an infrared image during administration of the ICG at high contract.

For example, in endoscopic submucosal dissection (hereinafter referred to as ESD) or the like for dissecting and peeling off a submucosa, in which a lesion site is present, using an endoscope, not to cut a relatively thick blood vessel in a mucosa with an electric knife or the like, a surgeon checks a position of such a blood vessel and performs treatment such as dissection.

SUMMARY OF THE INVENTION

An endoscope apparatus according to an aspect of the present invention includes: an illumination section configured to irradiate at least one or more illumination lights having a predetermined wavelength band on a subject; an image pickup section configured to pick up an image of return light from the subject based on irradiation by the illumination section; an image processing section configured to set a correction coefficient on the basis of change amounts concerning luminance values of a signal corresponding to a first wavelength band having a spectral characteristic of a narrowband and a signal corresponding to a second wavelength band having a spectral characteristic of a narrowband in which an absorption coefficient in the hemoglobin absorption characteristic is lower than the absorption coefficient of the signal corresponding to the first wavelength band and a scattering characteristic of the living tissue is suppressed more than the scattering characteristic of the signal corresponding to the first wavelength band between a wavelength band including a maximum value and a wavelength band including a minimum value on a hemoglobin light absorption characteristic of a living tissue of the subject and generate an image signal obtained by applying enhancement processing to the signal corresponding to the first wavelength band on the basis of the correction coefficient; and a display section configured to perform display of an image generated in the image processing section.

DETAILED DESCRIPTION OF THE PREFERRED EMBODIMENTS

Embodiments of the present invention are explained below with reference to the drawings.

First Embodiment (Configuration of an Endoscope Apparatus)

An embodiment of the present invention is explained below with reference to the drawings.

Figure 1:
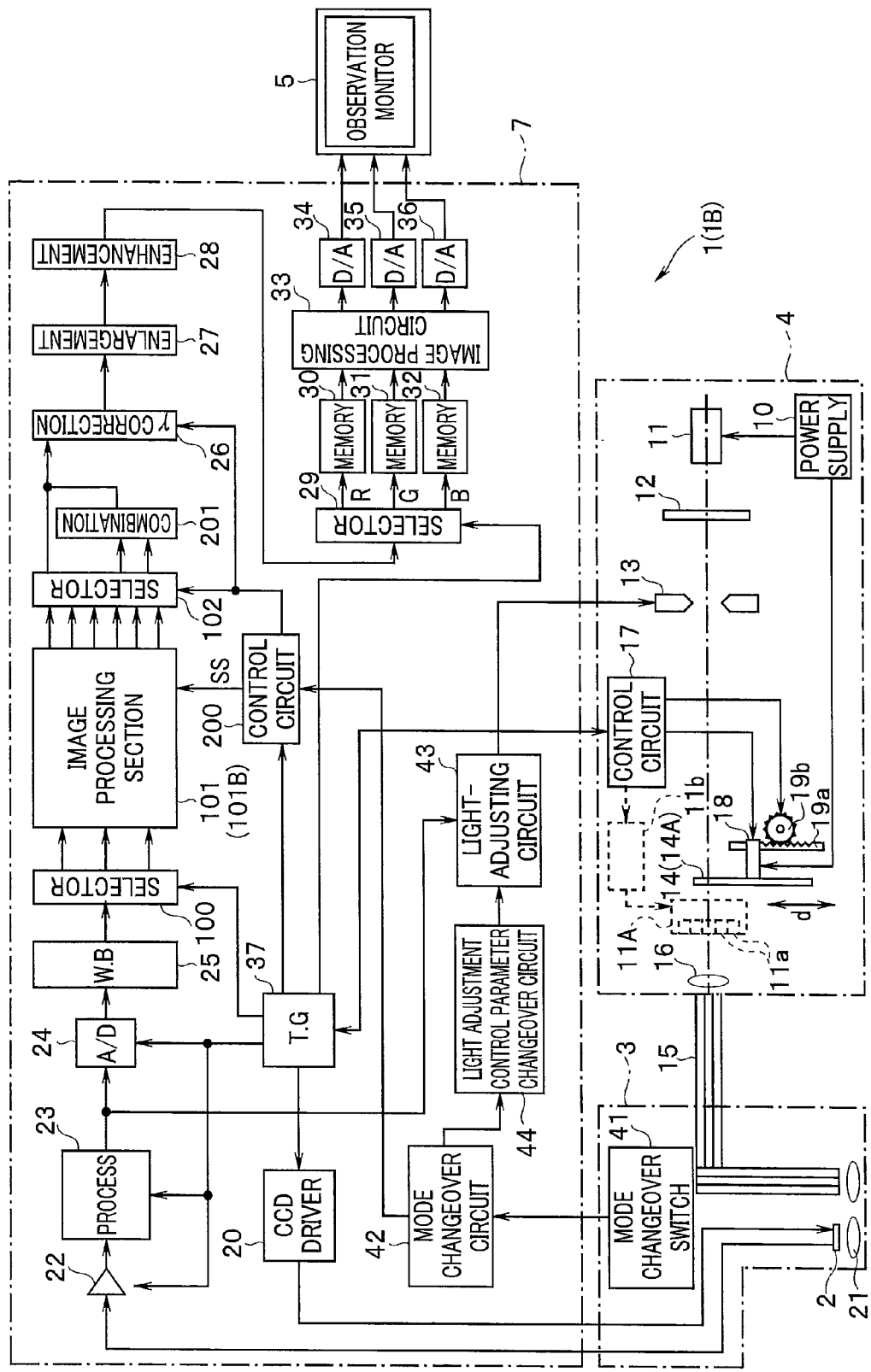
FIG. 1 is a configuration diagram showing a configuration of an endoscope apparatus according to a first embodiment of the present invention.

First, a configuration of an endoscope apparatus according to the present embodiment is explained. FIG. 1 is a configuration diagram showing the configuration of the endoscope apparatus according to the present embodiment.

As shown in FIG. 1, an endoscope apparatus 1 according to the present embodiment includes an electronic endoscope 3 including a CCD 2, which is an image pickup device, as living body image information acquiring means or a living body image information acquiring section inserted into a body cavity to pick up an image of an intra-body cavity tissue, a light source device 4 configured to supply illumination light to the electronic endoscope 3, and a video processor 7 configured to subject an image pickup signal from the CCD 2 of the electronic endoscope 3 to signal processing and display an endoscopic image on an observation monitor 5. The endoscope apparatus 1 has two modes, i.e., a normal light observation mode and a narrowband light observation mode. Note that, in the following explanation, the normal light observation mode of the endoscope apparatus 1 is the same as the normal light observation mode in the past. Therefore, explanation of a configuration of the normal light observation mode is omitted. The narrowband light observation mode is mainly explained.

The CCD 2 configures an image pickup section or image pickup means configured to receive return light of illumination light irradiated on a subject and pick up an image of the subject.

The light source device 4 functioning as illumination means or an illumination section includes a Xenon lamp 11 configured to emit illumination light (white light), a heat radiation cut filter 12 configured to cut off heat radiation of the white light, a diaphragm device 13 configured to control a light amount of the white light transmitted through the heat radiation cut filter 12, a rotating filter 14 functioning as band limiting means or a band limiting section configured to change the illumination light to frame-sequential light, a condensing lens 16 configured to condense the frame-sequential light, which is transmitted through the rotating filter 14, on an incident surface of a light guide 15 disposed in the electronic endoscope 3, and a control circuit 17 configured to control rotation of the rotating filter 14. The Xenon lamp 11, the rotating filter 14, and the light guide 15 configure an irradiating section or irradiating means configured to irradiate the illumination light on the subject.

Figure 2:
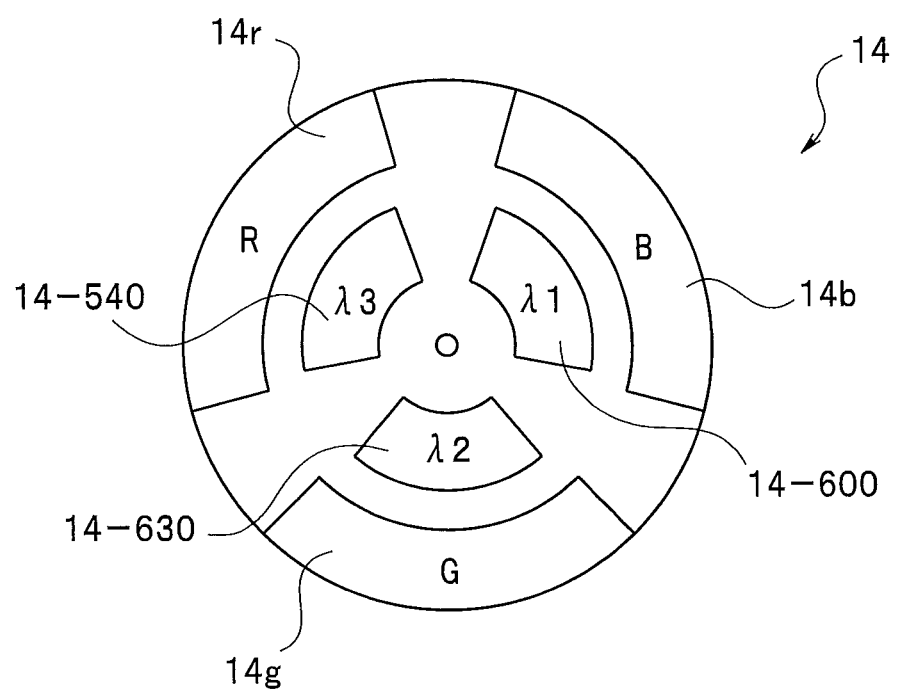
FIG. 2 is a diagram showing a configuration of a rotating filter 14 according to the first embodiment.

FIG. 2 is a diagram showing a configuration of the rotating filter 14. The rotating filter 14 is a filter configured to transmit light from the Xenon lamp 11, which is a light source. As shown in FIG. 2, the rotating filter 14 functioning as a wavelength band limiting section or wavelength band limiting means is configured in a disc shape and has a structure having a center as a rotation axis. The rotating filter 14 includes two filter groups. On an outer circumferential side of the rotating filter 14, an R (red) filter section 14r, a G (green) filter section 14g, and a B (blue) filter section 14b configuring a filter set for outputting frame-sequential light having a spectral characteristic for normal light observation are arranged along a circumferential direction as a first filter group.

On an inner circumferential side of the rotating filter 14, three filters 14-600, 14-630, and 14-540 configured to transmit lights having three predetermined narrowband wavelengths are arranged along the circumferential direction as a second filter group.

The filter 14-600 is configured to transmit light near a wavelength of 600 nm ($\lambda 1$) as narrowband light. The filter 14-630 is configured to transmit light near a wavelength of 630 nm ($\lambda 2$) as narrowband light. The filter 14-540 is configured to transmit light near a wavelength of 540 nm ($\lambda 3$) as narrowband light.

"Near" means that, in the case of "near a wavelength of 600 nm", narrowband light having center wavelength of 600 nm and having a distribution of width in a range of, for example, 20 nm centering on the wavelength of 600 nm (i.e., wavelength of 590 nm to 610 nm before and after the wavelength of 600 nm). The same holds true concerning the other wavelengths, i.e., the wavelength of 630 nm and the wavelength of 540 nm explained below.

The rotating filter 14 is arranged on an optical path extending from the Xenon lamp 11, which is an emitting section of the illumination light, to an image pickup surface of the CCD 2. In the respective modes, the rotating filter 14 limits at least two (here, three) among a plurality of wavelength bands of the illumination light to be narrowed.

The control circuit 17 controls a motor 18 for rotating the rotating filter 14 and controls the rotation of the rotating filter 14.

A rack 19a is connected to the motor 18. A not-shown motor is connected to a pinion 19b. The rack 19a is attached to be screwed in the pinion 19b. The control circuit 17 can move the rotating filter 14 in a direction indicated by an arrow "d" by controlling rotation of the motor connected to the pinion 19b. Therefore, the control circuit 17 controls, according to mode switching operation by a user explained below, the motor connected to the pinion 19b to locate the first filter group on the optical path in the normal light observation mode and locate the second filter group on the optical path in the narrowband light observation mode.

Note that electric power is supplied to the Xenon lamp 11, the diaphragm device 13, the rotating filter motor 18, and the motor (not shown in the figure) connected to the pinion 19b from a power supply section 10.

Therefore, the light source device 4 configures illumination means or an illumination section configured to irradiate at least one or more illumination lights (here, three narrowband lights) having a predetermined wavelength band on a subject in the narrowband light observation mode. Here, at least one (here, three) of the three illumination lights is narrowband light for highlighting a blood vessel in a deep part at 1 to 2 mm from a surface layer. The remaining one is narrowband light functioning as third illumination light that can be transmitted for a predetermined distance from a surface layer portion of the subject, here, by a range near the surface layer.

The video processor 7 includes a CCD driving circuit 20 functioning as a CCD driver, an amplifier 22, a process circuit 23, an A/D converter 24, a white balance circuit (hereinafter referred to as W. B) 25, a selector 100, an image processing section 101, a selector 102, a γ correction circuit 26, an enlarging circuit 27, an enhancing circuit 28, a selector 29, synchronizing memories 30, 31, and 32, an image processing circuit 33, D/A converters 34, 35, and 36, a timing generator (hereinafter referred to as T. G) 37, a mode changeover circuit 42, a light-adjusting circuit 43, and a light adjustment control parameter changeover circuit 44, a control circuit 200, and a combining circuit 201 functioning as display image generating means or a display image generating section.

The CCD driving circuit 20 drives the CCD 2 provided in the electronic endoscope 3 to cause the CCD 2 to output a frame-sequential image pickup signal synchronizing with the rotation of the rotating filter 14. The amplifier 22 amplifies a frame-sequential image pickup signal obtained by picking up an image of an intra-body cavity tissue with the CCD 2 via an objective optical system 21 provided at a distal end of the electronic endoscope 3.

The process circuit 23 applies correlated double sampling, noise removal, and the like to the frame-sequential image pickup signal amplified by the amplifier 22. The A/D converter 24 converts the frame-sequential image pickup signal processed by the process circuit 23 into a frame-sequential image signal of a digital signal.

The W. B 25 applies gain adjustment to the frame-sequential image signal digitized by the A/D converter 24 to equalize, for example, brightness of an R signal of the image signal and brightness of a B signal of the image signal with reference to a G signal of the image signal and executes white balance processing.

Note that white balance adjustment in the W. B 25 is performed with reference to luminance of return light of narrowband light near the wavelength of 600 nm.

The selector 100 outputs the frame-sequential image signal, which is received from the W. B 25 to be apportioned to respective sections in the image processing section 101.

The image processing section 101 is an image signal processing section or image signal processing means configured to convert RGB image signals for normal light observation or three image signals for narrowband light observation, which are received from the selector 100, into image signals for display. The image processing section 101 outputs image signals in the normal light observation mode and the narrowband light observation mode to the selector 102 according to a selection signal SS from the control circuit 200 based on a mode signal.

The selector 102 sequentially outputs a frame-sequential image signal of an image signal for normal light observation and an image signal for narrowband light observation, which are received from the image processing section 101, to the γ correction circuit 26 and the combining circuit 201.

The γ correction circuit 26 applies γ correction processing to the frame-sequential image signal received from the selector 102 or the combining circuit 201. The enlarging circuit 27 applies enlargement processing to the frame-sequential image signal subjected to the γ correction processing by the γ correction circuit 26. The enhancing circuit 28 applies edge enhancement processing to the frame-sequential image signal subjected to the enlargement processing by the enlarging circuit 27. The selector 29 and the synchronizing memories 30, 31, and 32 are sections for synchronizing the frame-sequential image signal from the enhancing circuit 28.

The image processing circuit 33 reads out respective frame sequential image signals stored in the synchronizing memories 30, 31, and 32 and performs moving image color shift correction processing and the like. The D/A converters 34, 35, and 36 convert an image signal received from the image processing circuit 33 into RGB analog video signals and output the RGB analog video signals to the observation monitor 5. The T. G 37 inputs a synchronization signal synchronizing with the rotation of the rotating filter 14 from the control circuit 17 of the light source device 4 and outputs various timing signals to the respective circuits in the video processor 7.

A mode changeover switch 41 for switching the normal light observation mode and the narrowband light observation mode is provided in the electronic endoscope 2. An output of the mode changeover switch 41 is outputted to the mode changeover circuit 42 in the video processor 7. The mode changeover circuit 42 of the video processor 7 is configured to output control signals to the light adjustment control parameter changeover circuit 44 and the control circuit 200. The light-adjusting circuit 43 is configured to control the diaphragm device 13 of the light source device 4 to perform proper brightness control on the basis of a light adjustment control parameter received from the light adjustment control parameter changeover circuit 44 and an image pickup signal processed by the process circuit 23.

The respective circuits in the video processor 7 execute predetermined processing corresponding to a designated mode. Processing corresponding to each of the normal light observation mode and the narrowband light observation mode is executed. A normal light observation image or a narrowband light observation image is displayed on the observation monitor 5. The observation monitor 5 is, as explained below, display means or a display section configured to perform image display on the basis of an enhanced and corrected image signal.

(Flow of Overall Processing of the Narrowband Light Observation)

Figure 3:
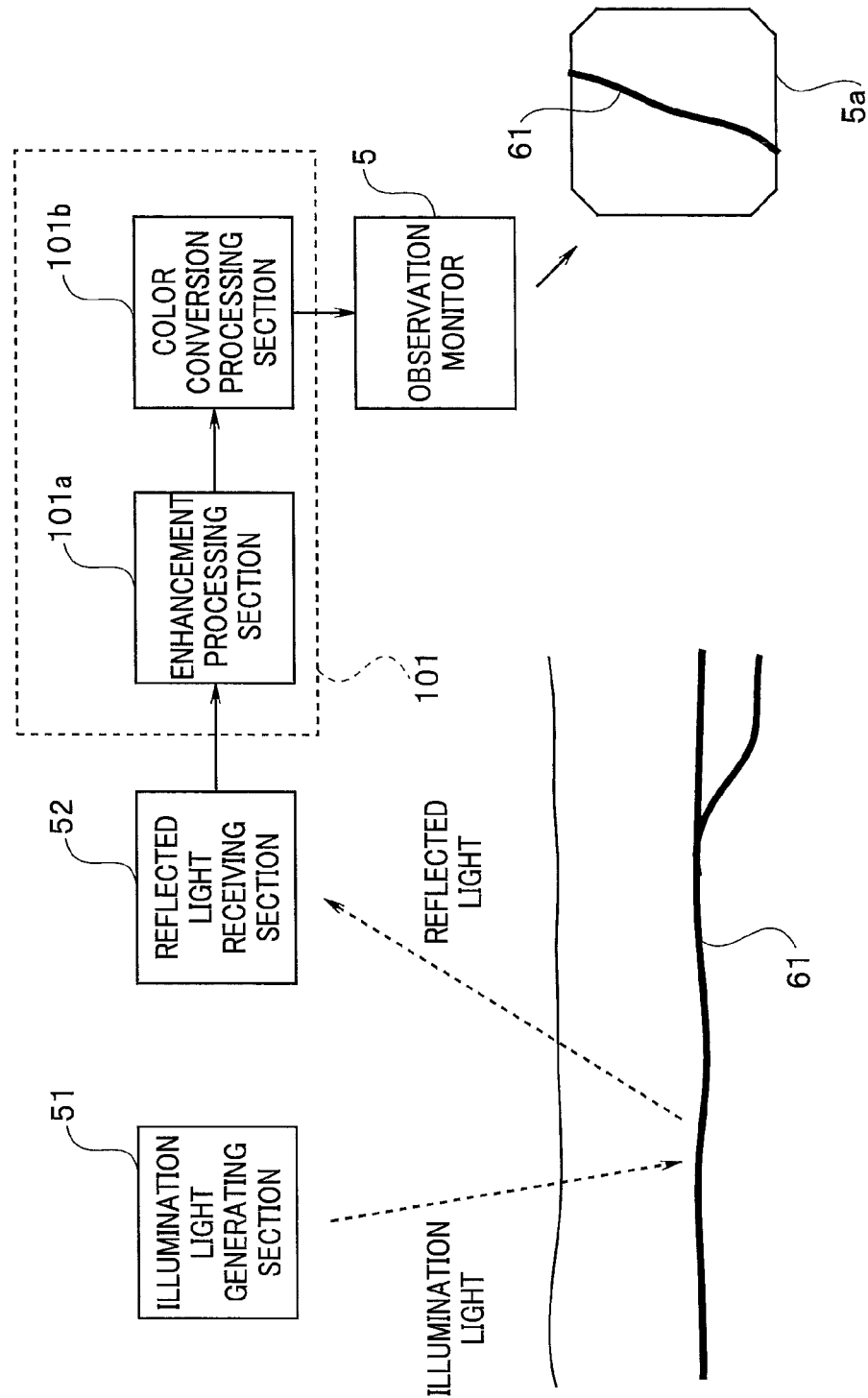
FIG. 3 is a diagram for explaining a flow of overall processing in narrowband light observation according to the first embodiment.

Next, an overall rough flow of narrowband light observation in the present embodiment is explained. FIG. 3 is a diagram for explaining a flow of overall processing in narrowband light observation according to the present embodiment.

A surgeon inserts an insertion portion of an endoscope into a body cavity and locates a distal end portion of the endoscope insertion portion near a lesion site under the normal light observation mode. Upon confirming a lesion site to be treated, in order to observe a relatively thick blood vessel in a deep part having a diameter of, for example, 1 to 2 mm running from a submucosa to a muscularis propria, the surgeon operates the mode changeover switch 41 to switch the endoscope apparatus 1 to the narrowband light observation mode.

Under the narrowband light observation mode, to emit light transmitted through the second filter group from the light source device 4, the control circuit 17 of the endoscope apparatus 1 controls the motor connected to the pinion 19b to move a position of the rotating filter 14. Further, the control circuit 200 controls the various circuits in the video processor 7 to perform image processing for observation by narrowband wavelength.

As shown in FIG. 3, in the narrowband light observation mode, illumination light having narrowband wavelength from an illumination light generating section 51 is emitted from a distal end portion of the insertion portion of the endoscope 3, transmitted through a mucosal layer, and irradiated on a blood vessel 61 running in the submucosa and the muscularis propria. Here, the illumination light generating section 51 includes the light source device 4, the rotating filter 14, the light guide 15 and the like and emits illumination light from a distal end of the endoscope insertion portion. According to the rotation of the rotating filter 14, narrowband light near a wavelength of 600 nm, narrowband light near a wavelength of 630 nm, and narrowband light near the wavelength of 540 nm are emitted from the light source device 4 continuously and in order and irradiated on an object.

Each of reflected lights of the narrowband light near the wavelength of 600 nm, the narrowband light near the wavelength of 630 nm, and the narrowband light near the wavelength of 540 nm is received by a reflected light receiving section 52, which is the CCD 2. The CCD 2 outputs an image pickup signal of each of the reflected lights. The image pickup signal is supplied to the selector 100 via the amplifier 22 and the like. The selector 100 retains, according to predetermined timing from the T. G 37, a first image signal P1 near the wavelength of 600 nm, a second image signal P2 near the wavelength of 630 nm, and a third image signal P3 near the wavelength of 540 nm and supplies the image signals to the image processing section 101. The image processing section 101 includes an enhancement processing section 101a and a color conversion processing section 101b for the narrowband light observation mode.

In ESD for dissecting and peeling off a submucosa of an inner wall of a digestive tract such as a stomach, an esophagus, or a large intestine in which a lesion site is present using the endoscope apparatus 1, the surgeon has to see to it that the surgeon does not cut a relatively thick blood vessel in a tissue with an electric knife or the like. When the surgeon sets the endoscope apparatus 1 in the narrowband light observation mode, the surgeon can clearly render a blood vessel under a surface of a living tissue.

In the enhancement processing section 101a of the image processing section 101 shown in FIG. 1, image processing explained below for image enhancement for the blood vessel 61 is performed. In the color conversion processing section 101b, respective image signals are allocated to respective channels for RGB of the observation monitor 5 and supplied to the selector 102. As a result, the relatively thick blood vessel 61 in the mucosa deep part is displayed on a screen 5a of the observation monitor 5 at high contrast. Therefore, the surgeon can apply the ESD to the lesion site while paying attention to the blood vessel 61 running in the submucosa and the muscularis propria, displayed on the observation monitor 5.

Figure 4:
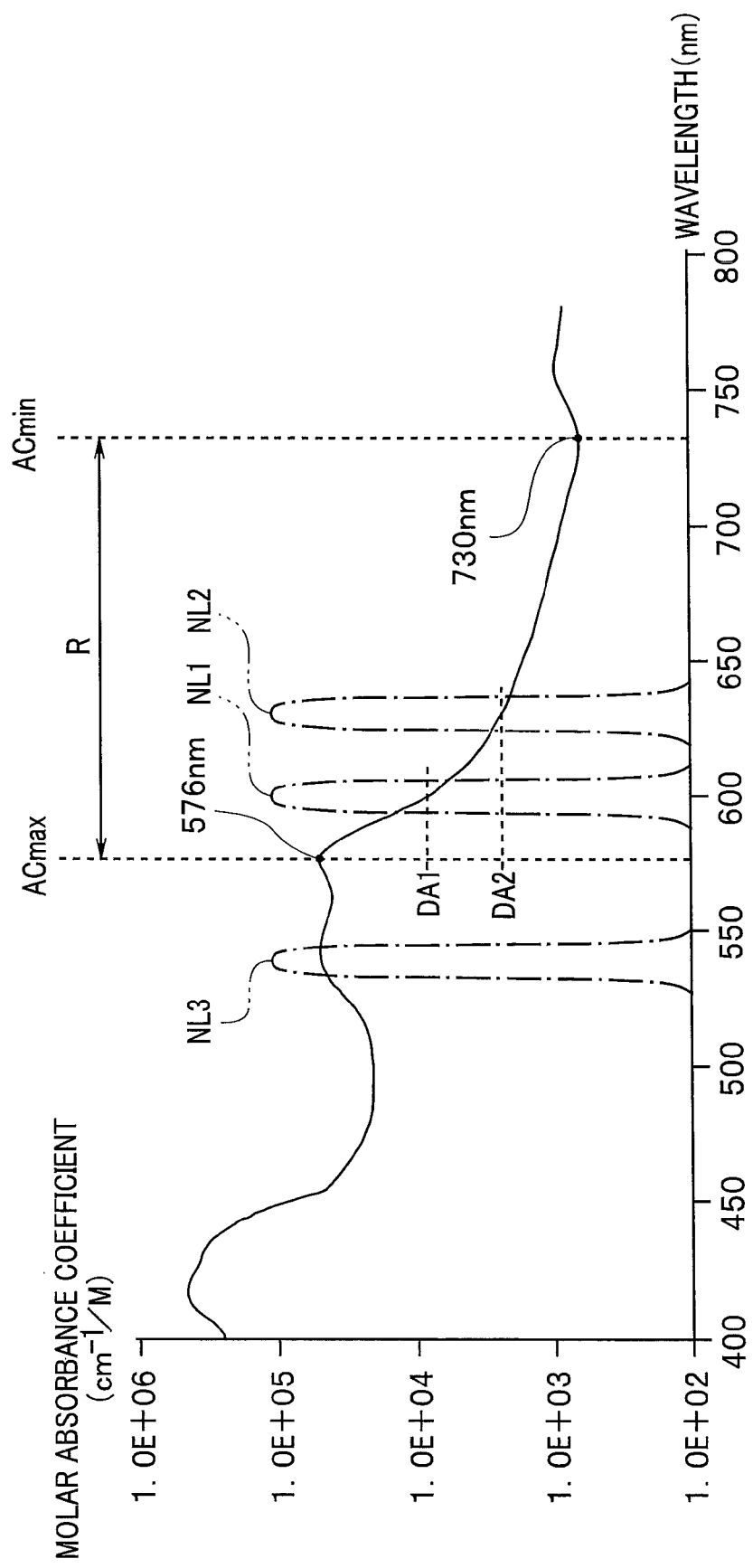
FIG. 4 is a diagram showing a light absorption characteristic of venous blood according to the first embodiment.

Here, a light absorption characteristic of venous blood is explained. FIG. 4 is a diagram showing the light absorption characteristic of the venous blood. An ordinate of FIG. 4 indicates a molar absorbance coefficient (cm$^{-1}$/M) and an abscissa indicates wavelength. Note that, although illumination lights of three narrowband lights are affected by a scattering characteristic of a living tissue itself, a scattering characteristic of the living tissue itself is a substantially monotonous decrease with respect to an increase in wavelength. Therefore, FIG. 4 is explained as an absorption characteristic of the living tissue.

In general, in the venous blood, hemoglobin oxide (HbO$_2$) and reduced hemoglobin (Hb) (hereinafter collectively simply referred to as hemoglobin) are contained at a ratio of about 60:40 to 80:20. Light is absorbed by the hemoglobin. However, an absorption coefficient of the light is different for each wavelength of the light. FIG. 4 shows a light absorption characteristic of the venous blood for each wavelength from 400 nm to about 800 nm. In a range from 550 nm to 750 nm, the absorption coefficient indicates a maximum value at a point of wavelength of about 576 nm and indicates a minimum value at a point of wavelength of 730 nm.

In the narrowband observation mode, three narrowband lights are irradiated. Return light of each of the narrowband lights is received by the CCD 2.

The narrowband light near the wavelength of 600 nm (hereinafter referred to as first narrowband light NL1) is light in a wavelength band within a wavelength band R of a maximum value ACmax of the absorption characteristic (here, an absorption coefficient at wavelength of 576 nm) to a minimum value ACmin (here, an absorption coefficient at wavelength of 730 nm) of the hemoglobin.

The narrowband light near the wavelength of 630 nm (hereinafter referred to as second narrowband light NL2) is also light within the wavelength band R from the maximum value ACmax to the minimum value ACmin of the absorption characteristic of the hemoglobin. However, the narrowband light is light in a wavelength band, wavelength of which is longer than the wavelength of the first narrowband light NL1, an absorption coefficient of which is lower than the absorption coefficient of the first narrowband light NL1, and a scattering characteristic of a living tissue of which is suppressed more than the scattering characteristic of the first narrowband light NL1. The suppressed scattering characteristic means that a scattering coefficient decrease toward a long wavelength side.

That is, the light source device 4 irradiates the first illumination light NL1 having a peak wavelength of a spectral characteristic between a wavelength band including the maximum value ACmax and the wavelength band at the minimum value ACmin in the absorption characteristic of the living tissue and the second illumination light NL2 having a peak wavelength of a spectral characteristic that a value in an absorption characteristic is lower than the value of the image signal P1 by the first illumination light NL1 and a scattering characteristic of the living tissue is suppressed more than the scattering characteristic of the first illumination light NL1.

The narrowband light near the wavelength of 540 nm (hereinafter referred to as third narrow-band light NL3) is light in a wavelength band outside the wavelength band R of the maximum value ACmax to the minimum value ACmin of the absorption characteristic of the hemoglobin and is illumination light that can be transmitted for a predetermined distance from a surface region portion of a mucosal surface of the subject.

The CCD 2 outputs image pickup signals for respective images of the three narrowband lights. Therefore, the respective images include a plurality of pixel signals based on respective return lights of the first, second, and third narrowband lights NL1, NL2, and NL3.

Figure 5:
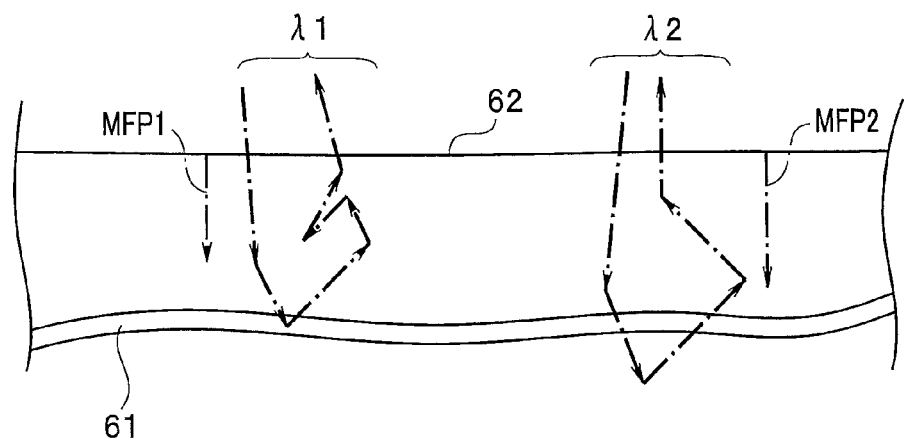
FIG. 5 is a diagram for explaining light propagation volumes in a living tissue of first narrowband light NL1 ($\lambda$1) and second narrowband light NL2 ($\lambda$2) according to the first embodiment.

Further, light propagation in the living tissue of the first narrowband light NL1 and the second narrowband light NL2, which are the illumination lights, is explained. FIG. 5 is a diagram for explaining a light propagation volume in the living tissue of the first narrowband light NL1 ($\lambda$1) and the second narrowband light NL2 ($\lambda$2). Each of the first narrowband light NL1 and the second narrowband light NL2 repeats a multiple scattering process in the living tissue. As a result, the first narrowband light NL1 and the second narrowband light NL2 are emitted from the mucosal surface as return lights. The first narrowband light NL1 and the second narrowband light NL2 respectively have mean free paths MFP1 and MFP2. The mean free path MFP1 of the first narrowband light NL1 is shorter than the mean free path MFP2 of the second narrowband light NL2.

As shown in FIG. 5, the first narrowband light NL1 having the wavelength of 600 nm ($\lambda$1) reaches near the blood vessel 61. The second narrowband light NL2 having the wavelength of 630 nm ($\lambda$2) reaches a position slightly deeper than the blood vessel 61. It is possible to perform highlighted display of a blood vessel image of a relatively deep part using such two narrowband lights and by performing enhancement processing explained below.

Therefore, lights satisfying requirements explained below are used as the two narrowband lights.

First, the two narrowband lights used in the present embodiment, i.e., the first narrowband light NL1 and the second narrowband light NL2 are relatively long-wave lights in a wavelength band of visible light in order to image the blood vessel 61 present in the deep part in the living tissue from a mucosal surface 62. Accordingly, both of the first narrowband light NL1 and the second narrowband light NL2 can reach near the blood vessel 61 present in the relatively deep part in the living tissue from the mucosal surface 62. Therefore, in the present embodiment, the narrowband light near the wavelength of 600 nm ($\lambda$1) is used as the first narrowband light NL1 and the narrowband light near the wavelength of 630 nm ($\lambda$2) is used as the second narrowband light NL2.

Further, the two narrowband lights used in the present embodiment, i.e., the first narrowband light NL1 and the second narrowband light NL2 are lights having a relatively small wavelength difference between the two narrowband lights. In other words, lights having a small difference between the mean free paths MFP1 and MFP2 of the two narrowband path, i.e., the first narrowband light NL1 and the second narrowband light NL2 are selected. The mean free path is an average traveling distance of light and is a function of a scattering coefficient.

Further, as the two narrowband lights used in the present embodiment, i.e., the first narrowband light NL1 and the second narrowband light NL2, lights having a relatively large difference in absorption between the two narrowband lights are selected, although the lights have a relatively small wavelength difference between the two narrowband lights. In the present embodiment, the narrowband light near the wavelength of 600 nm ($\lambda$1) is used as the first narrowband light NL1 and the narrowband light near the wavelength of 630 nm ($\lambda$2) is used as the second narrowband light NL2. As shown in FIG. 4, in a wavelength band equal to or larger than wavelength of 650 nm (e.g., near a wavelength of 700 nm), a difference between a molar absorbance coefficient DA1 of the first narrowband light NL1 and a molar absorbance coefficient DA2 of the second narrowband light NL2 is larger than a difference in absorption obtained when two narrowband lights having the same wavelength difference (e.g., 30 nm) (e.g., narrowband light near a wavelength of 700 nm and narrowband light near a wavelength of 730 nm) are selected.

That is, the two narrowband lights used in the present embodiment, i.e., the first narrowband light NL1 and the second narrowband light NL2 are lights having a relatively small wavelength difference between the two narrowband lights and relatively large difference in absorption between the two narrowband lights. By using such two narrowband lights, for example, capillaries at depth of several hundred microns from the surface layer, which are not desired to be displayed, are not displayed. Therefore, it is possible to highlight, with low noise, only a relatively thick blood vessel in a deep part of 1 to 2 mm, which is desired to be displayed. However, even if a wavelength difference between two narrow-band lights is large such as a wavelength difference between wavelength of 600 nm and wavelength of 680 nm, if a difference in absorption itself is large, it is possible to display a deep part blood vessel at high contrast in the same manner as the combination with the small wavelength (e.g., the wavelength of 600 nm and the wavelength of 630 nm).

Figure 34:
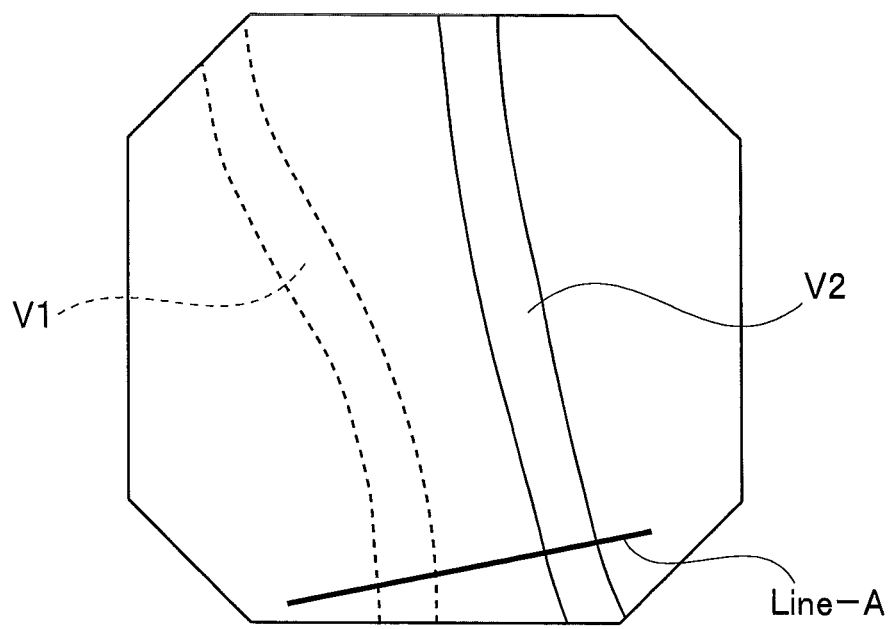
FIG. 34 is a schematic diagram of an image obtained by photographing an inside of an abdominal cavity of an animal using a spectral endoscope apparatus that can irradiate narrowband illumination light in time series at an interval of center wavelength of 10 nm.

FIG. 34 is a schematic diagram of an image obtained by photographing an inside of an abdominal cavity of an animal using a spectral endoscope apparatus capable of irradiating narrowband illumination light in time series at an interval of center wavelength of 10 nm. More specifically, an image in which respective monochrome images of 540 nm, 600 nm, and 630 nm are respectively allocated to a B channel, a G channel, and an R channel is shown. A blood vessel V1 and a blood vessel V2 in the image are thick blood vessels running from an upper left direction to a lower right direction in the image. The blood vessel V1 is deeper from a mucosal surface than the blood vessel V2. Here, monochrome images of fifteen patterns in total are photographed at a step of 10 nm from 540 nm to 680 nm.

Figure 35:
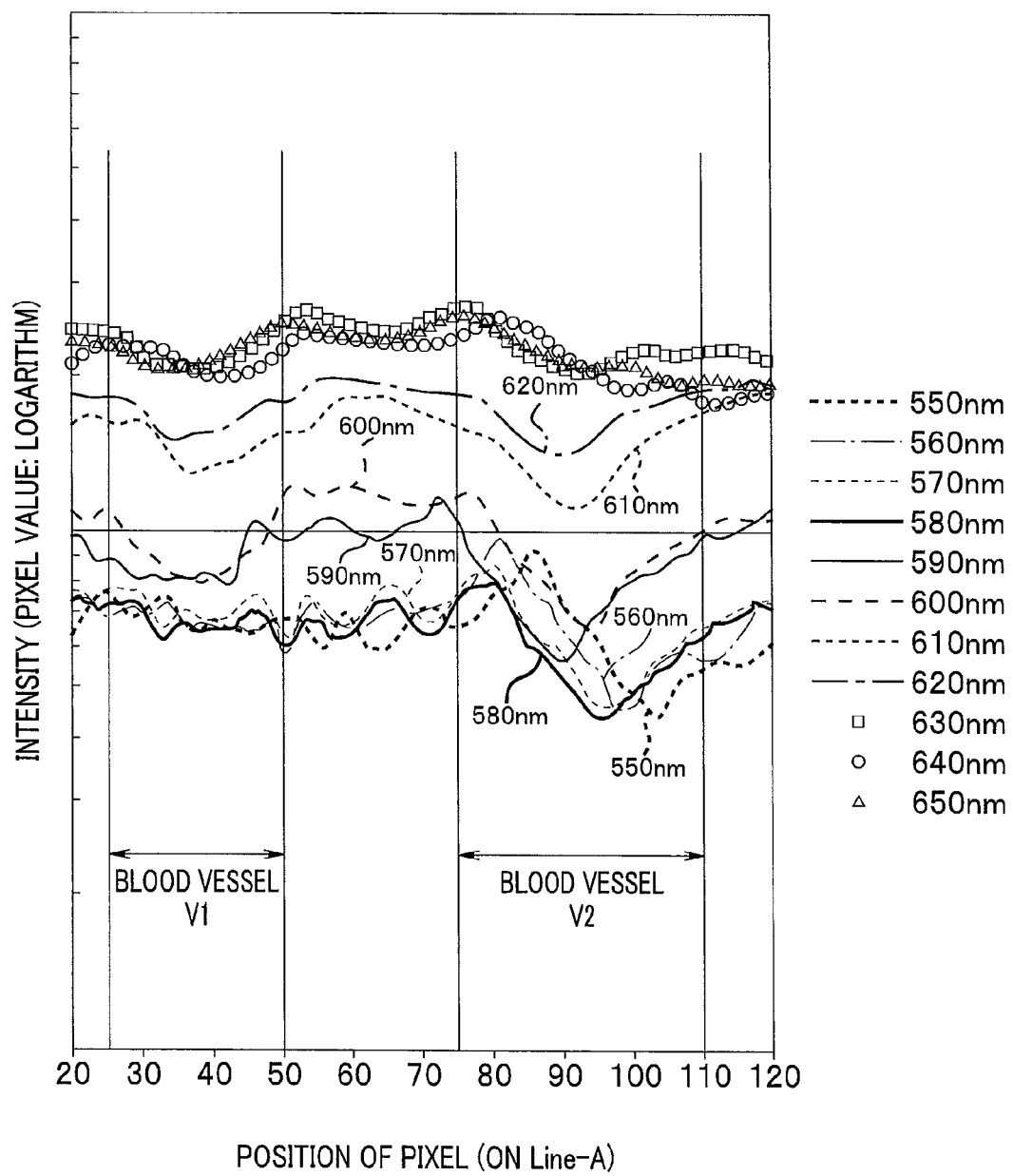
FIG. 35 is a graph in which, for a plurality of monochrome images shown in FIG. 34, intensities (logarithmically displayed pixel values) on a Line-A in respective images.

FIG. 35 is a graph in which, with respect to a plurality of monochrome images shown in FIG. 34, intensities (logarithmically displayed pixel values) on a Line-A in the respective images are shown on an ordinate. An abscissa in FIG. 35 indicates positions of pixels on the Line-A in the respective images. Positions of pixels of the blood vessel V1 are present near 25 to 50 and positions of pixels of the blood vessel V2 are present near 75 to 110. It is seen from FIG. 35 that illumination wavelengths at which the intensities attenuate in both the blood vessels, i.e., the blood vessel V2 present in a relatively shallow part and the blood vessel V1 located in a deep part, i.e., wavelengths at which illumination lights are intensely absorbed in the blood vessel V1 and the blood vessel V2 are about 590 nm to 620 nm.

Therefore, to detect blood vessels present from the relatively shallow part to the deep part, narrowband lights at about 590 nm to 620 nm are important wavelength information. The blood vessel V1 is present in a deep part of about 1 mm to 2 mm from the mucosal surface. Note that this experiment result substantially coincides with the theoretical calculation result by Beer-Lambert explained above (a relatively thick blood vessel can be displayed at high contrast by using narrowband lights at 15 nm before and after the wavelength of 600 nm).

As explained above, the illumination means or the illumination section including the light source device 4 irradiates the narrowband light NL1, which is the illumination light having the peak wavelength of the spectral characteristic between the wavelength band including the maximum value ACmax and the wavelength band at the minimum value ACmin in the absorption characteristic of the living tissue, and the narrowband light NL2, which is the illumination light having the peak wavelength of the spectral characteristic that the value in the absorption characteristic is lower than the value in the absorption characteristic of the return light by the narrowband light NL1 and the scattering characteristic of the living tissue is suppressed more than the scattering characteristic of the return light by the narrowband light NL1.

Further, the illumination means or the illumination section including the light source device 4 also irradiates the third illumination light NL3 that can be transmitted for the predetermined distance from the surface layer portion of the subject.

(Enhancement Processing of the Image Processing Section)

Figure 6:
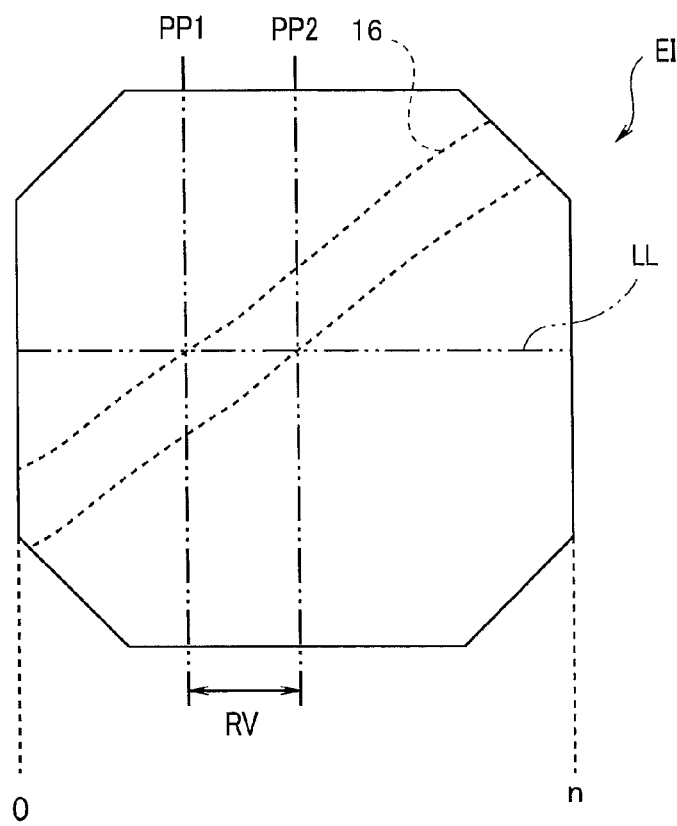
FIG. 6 is a diagram showing an example of an endoscopic image for explaining highlighting of a blood vessel in the endoscopic image according to the first embodiment.

Next, processing in the image processing section 101 is explained. FIG. 6 is a diagram showing an example of an endoscopic image for explaining highlighted display of a blood vessel in an endoscopic image.

In the normal light observation mode, in a picked-up endoscopic image EI, a blood vessel in a deep part of 1 to 2 mm from the surface layer portion is not displayed or is not easily displayed on the endoscopic image EI of the observation monitor 5.

On the other hand, in the narrowband light observation mode, when a blood vessel in a deep part is present in the picked-up endoscopic image EI, the blood vessel is displayed on the endoscopic image EI. Processing by the image processing section 101 is explained assuming that, as shown in FIG. 6, the blood vessel 61 (indicated by a dotted line) is present under a mucosal surface of a stomach.

Respective images by the two narrowband lights NL1 and NL2 are inputted to the image processing section 101. Each of the images is configured from a plurality of lines. Each of the lines includes a plurality of pixels.

The enhancement processing section 101a performs processing explained below for each line of the respective images. In the enhancement processing section 101a, to expand contrast of the blood vessel 61 in the deep part, an inter-band operation is performed concerning two images obtained by irradiation of the first narrowband light NL1 and the second narrowband light NL2.

Figure 7:
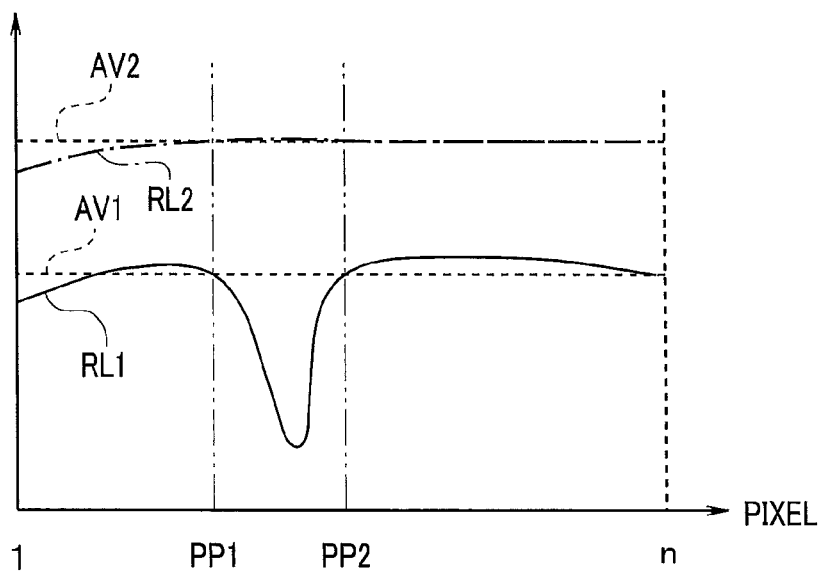
FIG. 7 is a diagram showing a luminance level of a pixel value of a certain line LL in FIG. 6.

The inter-band operation is explained using FIGS. 6 and 7. FIG. 7 is a diagram showing a luminance level of a pixel value of a certain line LL in FIG. 6. An abscissa of FIG. 7 indicates pixel positions arranged along a line direction in the endoscopic image EI and an ordinate indicates luminance values of pixels in the respective pixel positions. In FIG. 7, a luminance value distribution RL1 indicated by a solid line is a luminance profile, i.e., a luminance value distribution of return light of the first narrowband light NL1. A luminance value distribution RL2 indicated by an alternate long and short dash line is a luminance value distribution of return light of the second narrowband light NL2. Luminance of the luminance value distribution RL2 indicated by the alternate long and short dash line is higher than luminance of the luminance value distribution RL1 indicated by the solid line. This is because an absorption coefficient of hemoglobin of the second narrowband light NL2 is lower than the absorption coefficient of the first narrowband light NL1. Here, as shown in FIG. 6, the line LL includes n pixels from left. A range from pixel positions PP1 to PP2 on the line LL is a range in which the blood vessel 61 is present.

In this case, as shown in FIG. 7, in the luminance value distribution RL1 of the first narrowband light NL1, a luminance value is low in a range RV of the pixel positions PP1 to PP2 in which the blood vessel 61 is present. This is because the first narrowband light NL1 is intensely absorbed by hemoglobin of the blood vessel 61. In lines other than the line LL, a luminance value of the return light of the first narrowband light NL1 is also low in the range RV where the blood vessel 61 is present.

In the luminance value distribution RL2 of the second narrowband light NL2, as shown in FIG. 7, a luminance value is substantially the same in ranges including the range RV from the pixel positions PP1 to PP2 in which the blood vessel 61 is present. This is because the second narrowband light NL2 is transmitted through the blood vessel 1 and reaches an inside of a living tissue and returns without being much affected by absorption. In the lines other than the line LL, a luminance value of the return light of the second narrowband light NL2 is substantially the same in the ranges including the range RV in which the blood vessel 61 is present.

Note that, in FIG. 7, an average value of luminance values (hereinafter referred to as average luminance) of a plurality of pixels on the line LL concerning the return light of the first narrowband light NL1 is indicated by a dotted line AV1. An average luminance of luminance values of the plurality of pixels on the line LL concerning the return light of the second narrowband light NL2 is indicated by a dotted line AV2.

Therefore, the enhancement processing section 101a performs processing of the following Equation (1) concerning the respective pixels of each line shown in FIG. 7:

$$U = (Im(\lambda 1)/Im(\lambda 2)) \times K - 1 \quad \text{Equation (1)}$$

where, U represents a luminance ratio, Im represents luminance of each pixel, $Im(\lambda 1)$ represents a luminance value of the return light of the narrowband light near the wavelength of 600 nm ($\lambda 1$), $Im(\lambda 2)$ represents a luminance value of the return light of the narrowband light near the wavelength of 630 nm ($\lambda 2$), and K represents a correction coefficient. For example, a value of the following Equation (2) may be used as K:

$$K = (AVE(\lambda 2)/AVE(\lambda 1)) \quad \text{Equation (2)}$$

where, AVE represents average luminance of the respective lines, $AVE(\lambda 1)$ represents an average value of luminance values of the return light of the narrowband light near the wavelength of 600 nm ($\lambda 1$), and $AVE(\lambda 2)$ represents an average value of luminance values of the return light of the narrowband light near the wavelength of 630 nm ($\lambda 2$). In FIG. 7, the dotted line AV1 indicates a line of $AVE(\lambda 1)$ and the dotted line AV2 indicates a line of $AVE(\lambda 2)$.

Average luminance of two images obtained by the irradiation of the first narrowband light NL1 and the second narrowband light NL2 is adjusted by the correction coefficient K.

Figure 8:
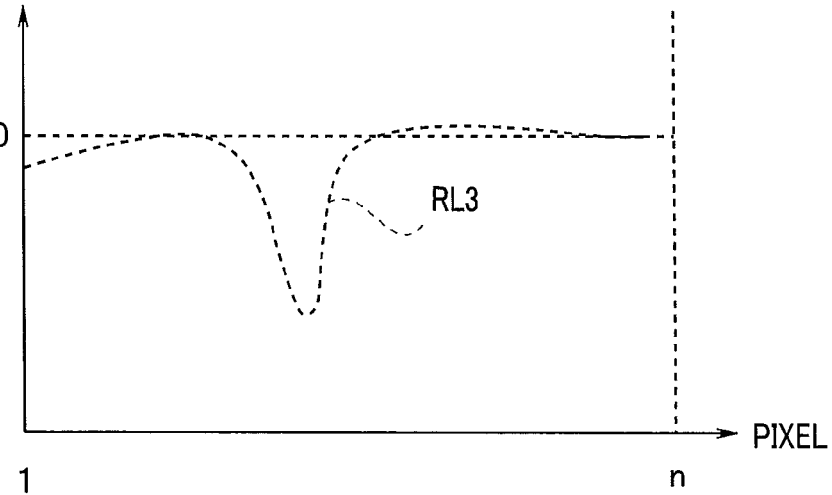
FIG. 8 is a diagram showing a level of a luminance ratio U of each pixel of the line LL in FIG. 6.

A luminance ratio U calculated according to the above Equation (1) in the line LL is as shown in FIG. 8. FIG. 8 is a diagram showing a level of the luminance ratio U of each pixel of the line LL in FIG. 6. An abscissa of FIG. 8 indicates the pixel positions arranged along the line direction in the endoscopic image EI and an ordinate indicates the luminance ratio U of the pixels in the respective pixel positions. Since minus 1 (−1) is included in Equation (1), a distribution of the luminance ratio U is a distribution with 0 set as a reference. That is, in FIG. 8, a luminance value distribution RL3 indicated by a dotted line can be considered as a distribution obtained by correcting the luminance value of the return light of the first narrowband light NL1.

A calculation by the following Equation (3) is applied to the luminance ratio U.

$$V = U \times R \quad \text{Equation (3)}$$

where, V represents a corrected luminance ratio and R represents an enhancement coefficient, which is a parameter for designating a blood vessel enhancement level.

Figure 9:
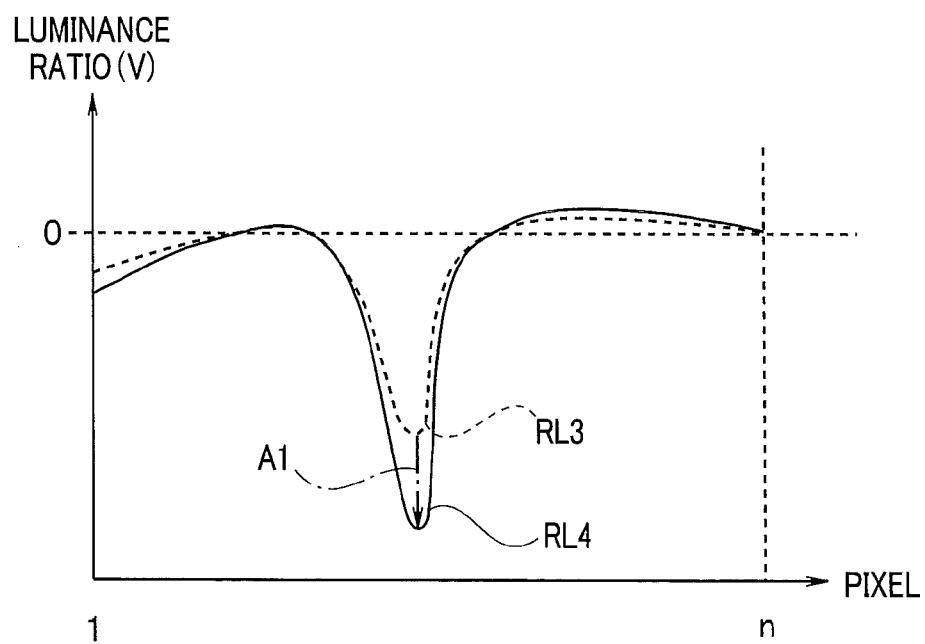
FIG. 9 is a diagram showing a level of an enhanced luminance ratio V of each pixel of the line LL in FIG. 6.

A luminance ratio V enhanced by the above Equation (3) in the line LL is as shown in FIG. 9. FIG. 9 is a diagram showing a level of the enhanced luminance ratio V of each pixel of the line LL in FIG. 6. An abscissa of FIG. 9 indicates the pixel positions arranged along the line direction in the endoscopic image EI and an ordinate indicates the luminance ratio U of the pixels in the pixel positions. That is, in FIG. 9, as indicated by an arrow A1 of an alternate long and short dash line, a luminance value distribution RL4 indicated by a solid line can be considered as a distribution obtained by performing correction for enhancing the luminance value distribution RL3 indicated by the dotted line.

A luminance value is calculated according to the following Equation (4) from the luminance ratio V calculated according to Equation (3).

$$ImA(\lambda 1) = Im(\lambda 1) \times (V+1) \quad \text{Equation (4)}$$

where, $ImA(\lambda 1)$ represents a luminance value after correction of a luminance value of return light of the narrowband light near the wavelength 600 nm ($\lambda 1$).

Figure 10:
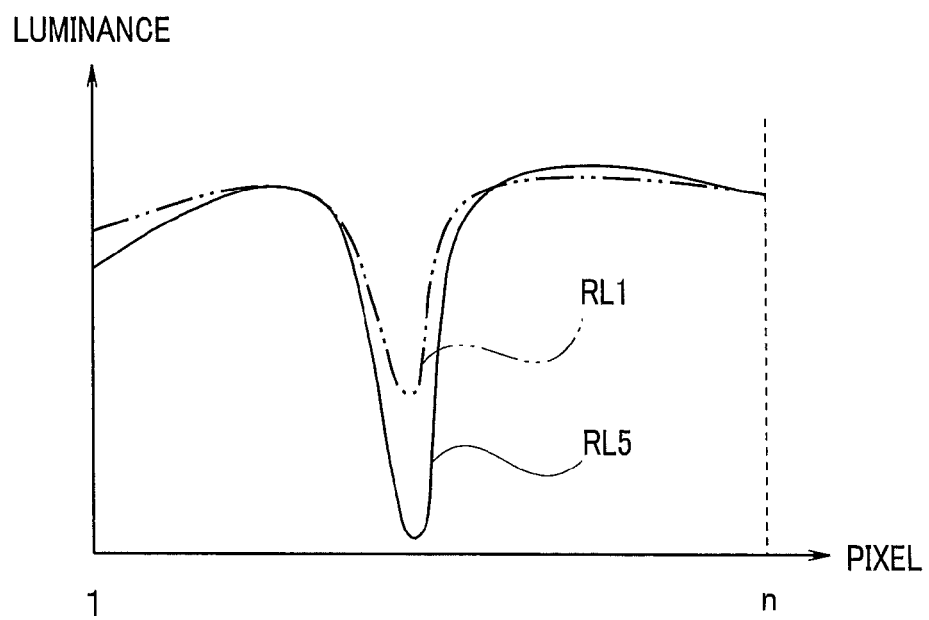
FIG. 10 is a diagram showing a level of an enhanced luminance value of return light of narrowband light near a wavelength of 600 nm ($\lambda$1) for each pixel of the line LL in FIG. 6.

The luminance value $ImA(\lambda 1)$ enhanced by the above Equation (4) in the line LL is as shown in FIG. 10. FIG. 10 is a diagram showing a level of an enhanced luminance value of the return light of the narrowband light near the wavelength of 600 nm ($\lambda 1$) of each pixel of the line LL in FIG. 6. An abscissa of FIG. 10 indicates the pixel positions arranged along the line direction in the endoscopic image EI and an ordinate indicates a luminance value AB of the pixels in the respective pixel positions. That is, in FIG. 10, a luminance value distribution RL5 indicated by a solid line can be considered as a distribution obtained by performing correction for enhancing a luminance value distribution RL1 indicated by an alternate long and two short dashes line. As a result, the enhancement processing section 101a outputs an enhanced corrected image signal BEP1 ($\lambda 1$) obtained by enhancing and correcting the first image signal P1 ($\lambda 1$) according to the inter-band operation.

Note that the enhancement processing may be performed according to a method explained below. In the enhancement processing explained above, enhancement of a blood vessel image is performed by calculating a ratio of luminance values of the respective pixels of the images having the two wavelengths and, for example, multiplying the luminance ratio with the correction coefficient. However, concerning the two images obtained by the irradiation of the first narrowband light NL1 and the second narrowband light NL2, enhancement of a blood vessel image may be performed by, for example, as indicated by the following Equation (5), performing division of respective pixel values and multiplying a pixel value obtained by the irradiation of the first narrowband light NL1 with a result of the division.

$$ImA1(\lambda 1) = Im(\lambda 1) \times (Im(\lambda 1)/Im(\lambda 2)) \quad \text{Equation (5)}$$

where, $ImA1(\lambda 1)$ represents a luminance value after correction of a luminance value of the return light of the narrowband light near the wavelength of 600 nm ($\lambda 1$).

Contrast of the blood vessel in the deep part can also be expanded by the enhancement processing performed using the division indicated by Equation (5).

Furthermore, the enhancement processing may be performed by processing explained below. Concerning the two images obtained by the irradiation of the first narrowband light NL1 and the second narrowband light NL2, enhancement of a blood vessel image may be performed by, for example, as indicated by the following Equation (6), performing subtraction of respective pixel values and multiplying a pixel value obtained by the irradiation of the first narrowband light NL1 with an absolute value of a result of the subtraction.

$$ImA2(\lambda 1)=Im(\lambda 1)\times |Im(\lambda 2)-Im(\lambda 1)| \quad \text{Equation (6)}$$

where, ImA2(λ1) represents a corrected luminance value of the return light of the narrowband light near the wavelength of 600 nm (λ1).

Contrast of the blood vessel in the deep part can also be expanded by the enhancement processing performed using the subtraction indicated by Equation (6).

Therefore, the image processing section 101a configures image processing means or an image processing section configured to generate, after the image pickup by the image pickup means or the image pickup section, an image signal enhanced and corrected by applying processing for enhancing the first image signal P1 (λ1) on the basis of a change amount, i.e., a difference between the first image signal P1 (λ1) having the peak wavelength of the spectral characteristic between the wavelength band including the maximum value ACmax and the wavelength band at the minimum value ACmin in the absorption characteristic of the living tissue and the second image signal P2 (λ2) having the peak wavelength of the spectral characteristic that the value in the absorption characteristic is lower than the value in the absorption characteristic of the first image signal P1 (λ1) and the scattering characteristic of the living tissue is suppressed more than the scattering characteristic of the first image signal P1 (λ1).

(Color Conversion Processing by the Image Processing Section)

Next, processing in the color conversion processing section 101b is explained. The second image signal P2 (λ2), the third image signal P3 (λ3), and the enhanced corrected image signal BEP1 (λ1) are inputted to the color conversion processing section 101b.

In the color conversion processing section 101b, processing for allocating the second image signal P2 (λ2), the third image signal P3 (λ3), and the enhanced corrected image signal BEP1 (λ1) to the RGB channels is performed.

Here, for example, the luminance value ImA(λ1) of the enhanced corrected image signal BEP1 (λ1), the luminance value Im(λ2) of the second image signal P2 (λ2), and the luminance value Im(λ3) of the third image signal P3 (λ3) are allocated to the RGB channels according to the following Equation (7):

$$\begin{pmatrix} B \\ G \\ R \end{pmatrix} = \begin{pmatrix} 1 & 0 & 0 \\ 0 & 1 & 0 \\ 0 & 0 & 1 \end{pmatrix} \begin{pmatrix} Im(\lambda 3) \\ ImA(\lambda 1) \\ Im(\lambda 2) \end{pmatrix} \quad \text{Equation (7)}$$

According to Equation (7), since the relatively large blood vessel 61 in the deep part is displayed in a rather reddish color, the surgeon can easily find the blood vessel 61.

Since the narrowband light near the wavelength of 540 nm is used as the third narrowband light NL3, capillaries and bleeding present in a relatively shallow region from the surface of the living tissue are displayed substantially in a yellow color.

Note that, in the color conversion processing section 101b, the following Equation (8) may be used instead of the above Equation (7):

$$\begin{pmatrix} B \\ G \\ R \end{pmatrix} = \begin{pmatrix} 1 & 0 & 0 \\ 1 & 0 & 0 \\ 0 & 1 & 0 \end{pmatrix} \begin{pmatrix} Im(\lambda 3) \\ ImA(\lambda 1) \\ Im(\lambda 2) \end{pmatrix} \quad \text{Equation (8)}$$

According to Equation (8), since the blood vessel 61 in the deep part is displayed in a slightly bluish color or a bluish green color and capillaries in the surface layer are displayed in a red to brown color, the surgeon can easily find the blood vessel 61 and the capillaries.

Furthermore, in the color conversion processing section 101b, the following Equation (9) may be used instead of the above Equation (7):

$$\begin{pmatrix} B \\ G \\ R \end{pmatrix} = \begin{pmatrix} 1 & 0 & 0 \\ 0.5 & 0.5 & 0 \\ 0 & 1 & 0 \end{pmatrix} \begin{pmatrix} Im(\lambda 3) \\ ImA(\lambda 1) \\ Im(\lambda 2) \end{pmatrix} \quad \text{Equation (9)}$$

Furthermore, in the color conversion processing 101b, the following Equation (10) may be used instead of the above Equation (7). Here, α takes a numerical value of about 1.0 to 1.5, β takes a numerical value of about 2.0 to 2.6, and γ takes a numerical value of about 2.5 to 3.3 (e.g., α:β:γ=0.56:1.00:1.17). In this case, since a tone of a deep part blood vessel is bluish green and a tone of a mucosa is similar to a tone in a normal observation, the surgeon can easily observe the blood vessel and the mucosa without stress. If α is set to a numerical value of about 2.3 to 2.7, β is set to a numerical value of about 2.3 to 2.7, and γ is set to a numerical value of about 1.7 to 2.1 (e.g., α:β:γ=1.00:1.00:0.76), it is easy to observe blood vessels in the surface layer and the deep part.

$$\begin{pmatrix} B \\ G \\ R \end{pmatrix} = \begin{pmatrix} \alpha & 0 & 0 \\ \beta & 0 & 0 \\ 0 & \gamma & 0 \end{pmatrix} \begin{pmatrix} Im(\lambda 3) \\ ImA(\lambda 1) \\ Im(\lambda 2) \end{pmatrix} \quad \text{Equation (10)}$$

Note that another example of the channel allocation in the color conversion processing section 101b is explained. For example, during medical treatment, instead of the above Equation (7), the narrowband light near the wavelength of 540 nm may be allocated to the B channel, the narrowband light near the wavelength 630 nm may be allocated to the G channel, and the narrowband light near the wavelength 600 nm (i.e., the enhanced corrected image signal BEP1 (λ1)) may be allocated to the R channel.

Further, during diagnoses, the narrowband light near the wavelength of 540 nm may be allocated to the B channel and the G channel and the narrowband light near the wavelength of 600 nm or the narrowband light near the wavelength of 630 nm may be allocated to the R channel.

Here, color balance adjustment is explained. For example, when the narrowband light near the wavelength of 540 nm is allocated to the B channel, the narrowband light near the wavelength of 600 nm is allocated to the G channel, and the narrowband light near the wavelength of 630 nm is allocated to the R channel as in the Equation (7), it is desirable to amplify a signal of the B channel with respect to a signal of the R channel. Signal intensity of the narrowband light near the wavelength of 600 nm is not corrected. The two signals are adjusted such that signal intensity of the narrowband light near the wavelength of 540 nm allocated to the B channel is 0.7 to 2.5 times as high as signal intensity of the narrowband light near the wavelength of 630 nm allocated to the R channel. Note that the color conversion processing may be performed after the color balance adjustment is performed or the color balance processing may be performed after the color conversion processing.

Consequently, differences of tones among a mucosa, a fiber tissue having a white tone, yellow bleeding, a black carbonized region, and a thick blood vessel having a tone of red to magenta become more conspicuous. Therefore, it is possible to obtain a display image with which the surgeon can more easily perform treatment or a diagnosis.

A color balance adjusting circuit for such color balance adjustment may be provided at a pre-stage of the W. B 25 shown in FIG. 1. In that case, when intensities of illumination lights of the narrowband light near the wavelength of 540 nm and the narrowband light near the wavelength of 630 nm are substantially equal, the color balance adjusting circuit multiplies a signal of the narrowband light near the wavelength of 540 nm allocated to the B channel with about 0.7 to 1.5 and multiplies a signal of the narrowband light near the wavelength of 630 nm allocated to the R channel with about 0.6 to 1.0.

Note that the color balance adjustment may be performed in the color conversion processing section 101b, may be performed by adjusting intensity of illumination light in the light source device 4, or may be performed by adjusting transmittances of respective colors of a color filter of the image pickup device.

(Flow of Overall Processing in the Image Processing Section)

Figure 11:
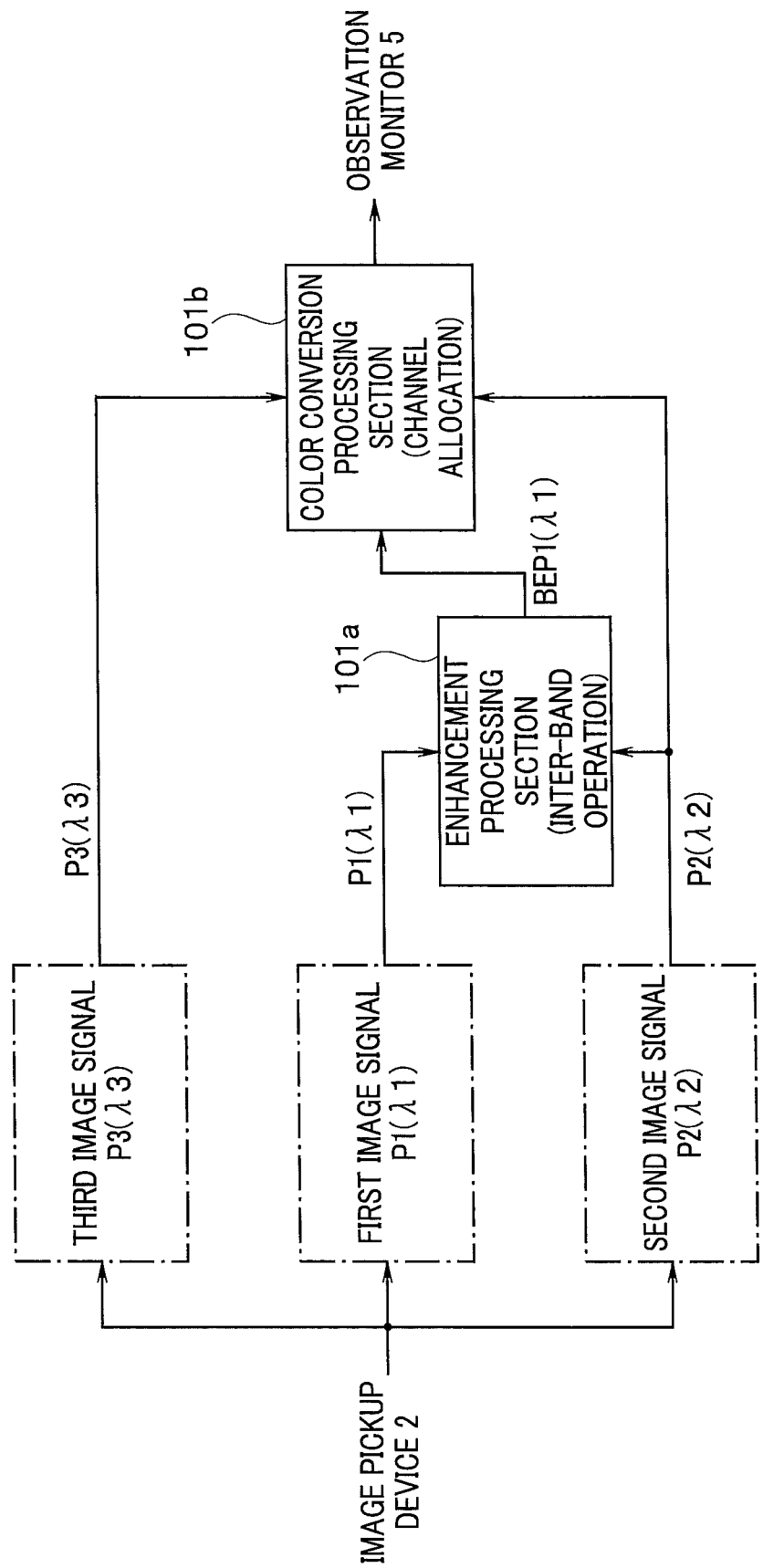
FIG. 11 is a diagram for explaining a flow of processing for an image obtained from an image pickup device 2 in an image processing section 101 according to the first embodiment.

Next, a flow of processing for an image obtained from the image pickup device 2 in the image processing section 101 is explained. FIG. 11 is a diagram for explaining a flow of the processing for an image obtained from the image pickup device 2 in the image processing section 101.

As shown in FIG. 11, three images from the image pickup device 2 are inputted to the image processing section 101 as the first to third image signals P1, P2, and P3. In the enhancement processing section 101a, the enhancement processing by the inter-band operation is applied to the two image signals P1 and P2 among the inputted three images. The color conversion processing section 101b applies the color conversion processing by the channel allocation to the second image signal P2 and the third image signal P3 and the enhanced corrected image signal BEP1 (λ1) obtained by the enhancement processing and outputs the signals to the observation monitor 5.

As explained above, the two narrowband lights having the absorption characteristic explained above between the maximum value and the minimum value of the absorption characteristic of the living tissue shown in FIG. 4 are irradiated on a living body mucosa and the enhancement processing is applied to an image of obtained two return lights of the narrowband lights. Consequently, a relatively thick blood vessel present in a relatively deep part of the living body mucosa is highlighted and displayed on the screen of the observation monitor 5. Therefore, the surgeon can perform desired treatment such as ESD while looking at and checking the relatively thick blood vessel as well.

In the endoscope apparatus 1 explained above, a blood vessel present in a portion close to a surface layer portion of the living body mucosa can also be displayed using the third narrowband light NL3.

For example, since the third narrowband light NL3 near the wavelength of 540 nm is used, a state of capillaries of the surface layer portion is also displayed on the screen of the observation monitor 5 simultaneously with the thick blood vessel. Therefore, the surgeon can use an endoscopic image on the screen of the observation monitor 5 not only for treatment but also for performing, from a state of capillaries, for example, a degree of a concentration degree or a dispersion degree of the capillaries, a diagnosis of a living body tissue, for example, a presence diagnosis of cancer or a range diagnosis for specifying a range of cancer and a discrimination diagnosis for determining whether a diseased part is benign or malignant. Further, the surgeon can also perform, for example, a penetration depth diagnosis with consciousness directed to a blood vessel of a deeper part.

Note that the light source device 4 explained above generates illumination light in a desired wavelength band using the Xenon lamp 11, the rotating filter 14, and the like. However, in the endoscope apparatus 1, as indicated by a dotted line, the light source device 4 may be configured to include a light emitting section 11A including a light emitting diode group 11a formed by a plurality of light emitting diodes (LEDs) that emit desired wavelengths, for example, respective wavelengths of RGB corresponding to the first filter group and respective wavelengths near 600 nm and near 630 nm corresponding to the second filter group. In that case, the light emitting section 11A and the light guide 15 configure an irradiating section configured to irradiate illumination light on an object.

For example, in FIG. 1, the light emitting section 11A indicated by the dotted line is provided in the light source device 4 instead of the Xenon lamp 11, the heat radiation cut filter 12, the diaphragm device 13, the rotating filter 14, and the like. Further, in the light source device 4, a driving circuit 11b for driving the light-emitting diodes of the light emitting section 11A at predetermined timing according to the respective modes is provided. The light emitting section 11A including a plurality of LEDs 11a receives power supply from a power supply 10. The light emitting section 11A is controlled and driven by the driving circuit 11b under a control signal from the control circuit 17.

Even when the endoscope apparatus 1 explained above is configured using such a light source device, it is possible to obtain effects same as the effects explained above.

Note that as the light emitting section 11A, a laser diode (LD) configured to emit a predetermined plurality of narrowband lights may be used.

Irrespective of which of a Xenon light source, an LED, and an LD is mounted on the light source device or even when the CCD 2 is not the monochrome image pickup device and an RGB color filter or a color filter of a complementary color system functioning as wavelength band limiting means or a wavelength band limiting section are provided, it is possible to obtain effects same as the effects explained above.

The second narrowband light NL2 shown in FIG. 4 may be light in a longer wavelength band than the minimum value ACmin (here, the absorption coefficient at the wavelength of 730 nm) of the absorption characteristic of hemoglobin. That is, the wavelength of the second narrowband light NL2 is in a wavelength band in which an absorption coefficient is lower than the absorption coefficient of the wavelength of the first narrowband light NL1 and a scattering characteristic of a living body tissue is suppressed more than the scattering characteristic of the wavelength of the first narrowband light NL1. For example, even when 740 nm, 770 nm, 805 nm, 810 nm, 850 nm, 870 nm, 880 nm, 910 nm, 940 nm, 1020 nm, and 1300 nm are used, it is possible to obtain effects equivalent to the effects explained above (e.g., when the narrowband light NL2 is set to any one of the wavelengths of 740 nm to 1300 nm, the narrowband light NL1 is set to any wavelength equal to or higher than 576 nm and at least equal to or lower than 630 nm). Note that the second narrowband light NL2 can be generated irrespective of which of the Xenon light source, the LED, and the LD is mounted as the light source device.

As explained above, according to the present embodiment, it is possible to provide an endoscope apparatus that can clearly display a blood vessel in a mucosa deep part without performing complicated work of drug administration.

Second Embodiment

In the first embodiment, at least one narrowband light is actually irradiated on a living body tissue as illumination light and the enhancement processing explained above is applied to an image of return light of the illumination light. However, in the present embodiment, at least one narrowband light is not actually irradiated on a living body tissue, image information of return lights of respective narrowband lights is obtained by so-called spectral estimation, and the enhancement processing explained above is applied to spectral image signals having respective wavelengths obtained by the spectral estimation. That is, in the first embodiment explained above, the first and second narrowband lights NL1 and NL2 are generated by the lighting device including the rotating filter or the light emitting device such as the light emitting diode and the enhancement processing is applied to images of return lights of the first and second narrowband lights NL1 and NL2. However, in the present embodiment, image signals corresponding to the first and second narrowband lights NL1 and NL2 are obtained by the spectral estimation processing and the enhancement processing is applied to spectrally estimated image signals obtained by the spectral estimation.

Figure 12:
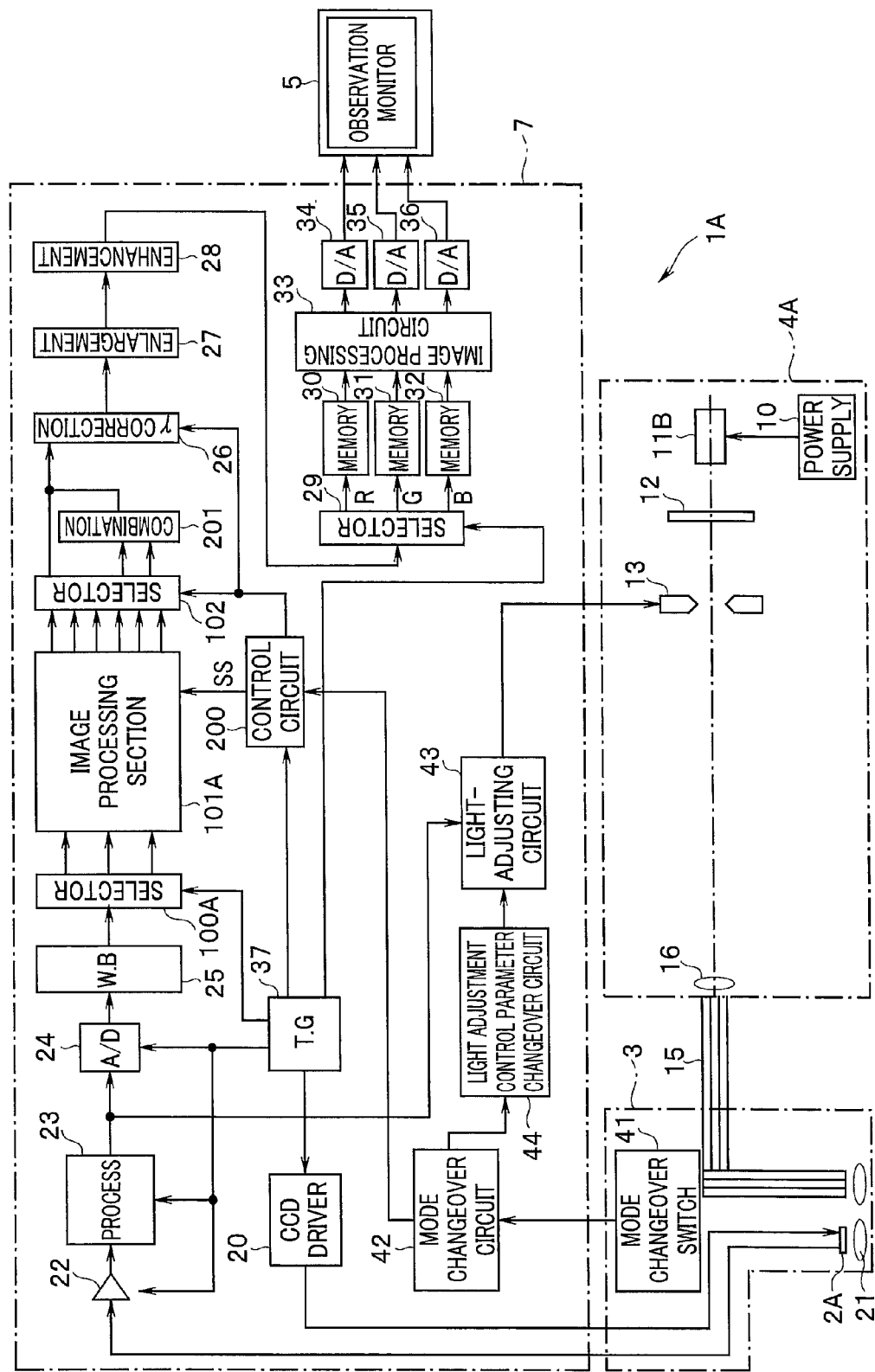
FIG. 12 is a configuration diagram showing a configuration of an endoscope apparatus 1A according to a second embodiment.

FIG. 12 is a configuration diagram showing a configuration of an endoscope apparatus 1A according to the second embodiment. In FIG. 12, components same as the components shown in FIG. 1 are denoted by the same reference numerals and signs and explanation of the components is omitted.

As shown in FIG. 12, a light source device 4A includes a lamp 11B configured to emit white light, the heat radiation cut filter 12, and the diaphragm device 13. Illumination light from the light source device 4A is irradiated on an object via the light guide 15. Note that the lamp 11B may be a lamp that emits light other than the white light.

An image pickup device 2A provided at a distal end of an insertion portion of the endoscope 3 is a color image pickup device. The image pickup device 2A is, for example, a color CCD. The image pickup device 2A includes an RGB color filter on an image pickup plane. Return light from the object is received by respective pixel sections of the image pickup plane via the RGB color filter, which is wavelength band limiting means or a wavelength band limiting section. Image signals of three colors of RGB are outputted from the image pickup device 2A.

A selector 100A outputs the three image signals of RGB to an image processing section 101A. The image processing section 101A includes a spectral estimation section. In the narrowband light observation mode, the image processing section 101A outputs a spectrally estimated image signal near a wavelength of 600 nm, a spectrally estimated image signal near a wavelength of 630 nm, and a spectrally estimated image signal near a wavelength of 540 nm.

Figure 13:
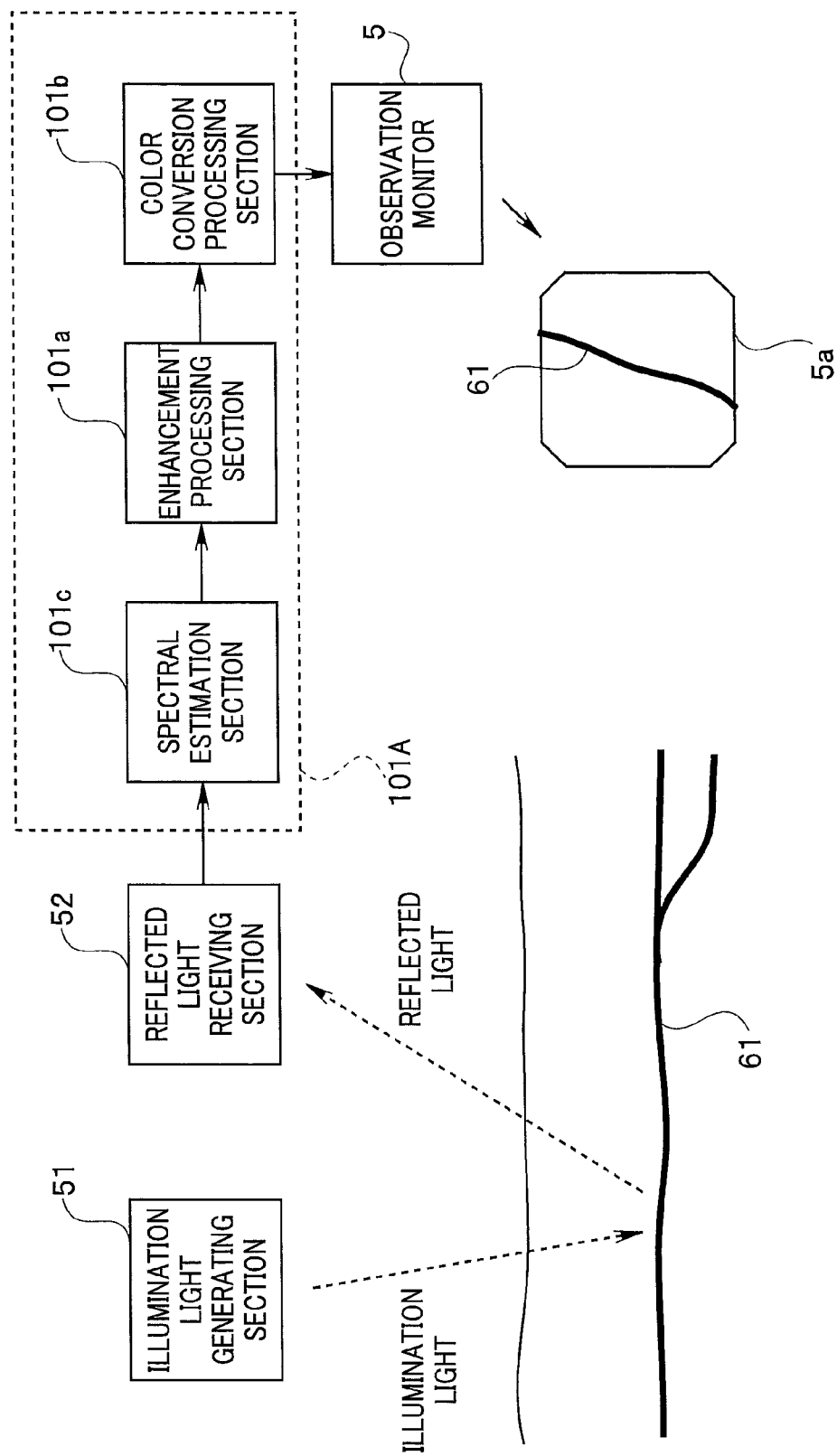
FIG. 13 is a diagram for explaining a flow of overall processing in narrowband light observation according to the second embodiment.

FIG. 13 is a diagram for explaining a flow of overall processing in narrowband light observation according to the present embodiment. In FIG. 13, components same as the components shown in FIG. 3 are denoted by the same reference numerals and signs and explanation of the components is omitted. The image processing section 101A includes a spectral estimation section 101c in addition to the enhancement processing section 101a and the color conversion processing section 101b. The spectral estimation section 101c extracts, from the three images of RGB, a first spectrally estimated image signal e1 near the wavelength of 600 nm, a second spectrally estimated image signal e2 near the wavelength of 630 nm, and a third spectrally estimated image signal e3 near the wavelength of 540 nm according to spectral estimation processing and outputs the spectrally estimated image signals to the enhancement processing section 101a.

More specifically, the spectral estimation section 101c calculates, according to a matrix operation, an n-dimensional spectral image from the three inputs on the basis of a priori information given in advance and selectively outputs e1, e2, and e3 out of a calculated n-dimensional spectrally estimated image signal. The spectral estimation section 101c is configured to calculate, using the matrix operation or the like, the spectrally estimated image signal e1 near the wavelength of 600 nm, the spectrally estimated image signal e2 near the wavelength of 630 nm, and the third estimated image signal e3 near the wavelength of 540 nm and output the spectrally estimated image signals.

Subsequent processing in the enhancement processing section 101a and the color conversion processing section 101b concerning the first, second, and third spectrally estimated image signals outputted from the spectral estimation section 101c is the same as the processing explained in the first embodiment.

Figure 14:
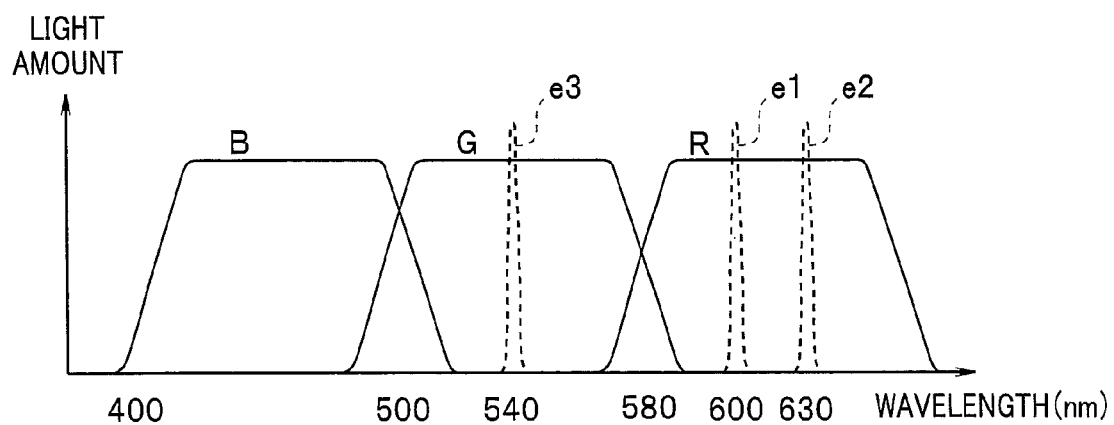
FIG. 14 is a diagram showing a spectral characteristic for explaining a case in which spectral image signals e1, e2, and e3 of three narrowband lights are estimated from image signals B, G, and R of three wideband lights according to the second embodiment.

FIG. 14 is a diagram showing a spectral characteristic for explaining a case in which spectral image signals e1, e2, and e3 of three narrowband lights are estimated from image signals B, G, R of three wideband lights. The three wideband lights B, G, R in FIG. 14 are obtained by a color filter of the image pickup device 2A. Image signals of the three wideband light B, G, and R are inputted to the spectral estimation section 101c.

The spectral estimation section 101c estimates, according to the spectral estimation processing, the spectrally estimated image signals e1, e2, and e3 of the three narrowband lights from the image signals B, G, R of the three wideband lights. The spectrally estimated image signal e1 of the narrowband light near the wavelength of 600 nm, the spectrally estimated image signal e2 of the narrowband light near the wavelength of 630 nm, and the spectrally estimated image signal e3 of the narrowband light near the wavelength of 540 nm are obtained from the image signals B, G, and R of the wideband lights having wavelength bands shown in FIG. 14 according to the spectral estimation processing. Here, the spectrally estimated image signals e1 and e2 of two narrowband lights within the wavelength band R from the maximum value ACmax to the minimum value ACmin in FIG. 4 and the spectrally estimated image signal e3 of the narrowband light outside the wavelength band R are obtained by spectral estimation. The spectrally estimated image signals e1, e2, and e3 are supplied to the enhancement processing section 101a.

Note that at least the two spectrally estimated image signals e1 and e2 (here, the three spectrally estimated image signals e1, e2, and e3) may be obtained from image signals of the two wideband lights among the three wideband lights, for example, image signals of the wideband lights G and R according to the spectral estimation processing.

Furthermore, image signals of the three (or two) wideband lights may be obtained by irradiating, in the light source device, return lights of three (or two) illumination lights, which are generated by arranging first group filers of a rotating filter having a sensitivity characteristic with which the image signals having the spectral characteristic shown in FIG. 14 are obtained, on a monochrome image pickup device rather than obtaining the image signals using a color filter of a color image pickup device.

As explained above, the spectral estimation section 101c generates at least two spectrally estimated image signals e1 and e2 on the basis of the at least two image pickup signals of return light of the subject according to the spectral estimation processing and outputs the spectrally estimated image signals e1 and e2. Further, the spectral estimation section 101c also generates, on the basis of the at least two image pickup signals, the spectrally estimated image signal e3 corresponding to return light based on irradiation of illumination light, which can be transmitted for a predetermined distance from a surface layer portion of the subject, according to the spectral estimation processing and outputs the spectrally estimated image signal e3. As explained above, the processing in the enhancement processing section 101a and the color conversion processing section 101b is the same as the processing in the first embodiment.

Therefore, effects same as the effects of the endoscope apparatus 1 can be obtained by the endoscope apparatus 1A in the present embodiment as well.

Next, a modification concerning the spectral estimation is explained.

In the processing of the spectral estimation explained above, spectral image signals of a plurality of narrowband lights are estimated from image signals of a plurality of wideband lights. However, the processing is not limited to such a method and may be methods explained below.

A first method is a method of estimating three spectral image signals from image signals of two wideband lights and an image signal of one narrowband light. Since the image signal of the narrowband light is used, it is possible to improve accuracy of the spectral estimation.

Figure 15:
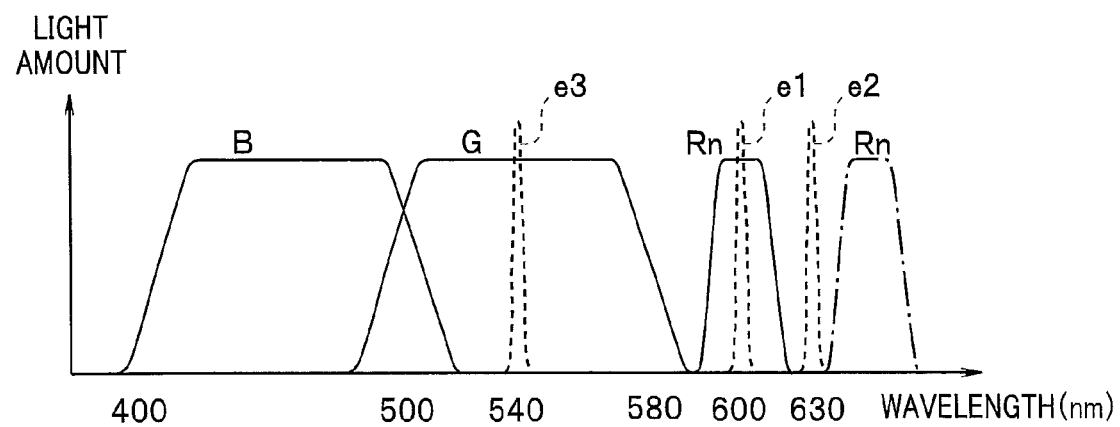
FIG. 15 is a diagram showing a spectral characteristic for explaining a case in which spectral image signals of three narrowband lights are estimated from image signals of two wideband lights and an image signal of one narrowband light according to the second embodiment.

FIG. 15 is a diagram showing a spectral characteristic for explaining a case in which spectral image signals of three narrowband lights are estimated from image signals of two wideband lights and an image signal of one narrowband light. As shown in FIG. 15, wideband lights are used for B and G and narrowband light is used for R. The spectral estimation section 101c estimates the three spectrally estimated image signals e1, e2, and e3 from image signals B and G of two wideband lights and an image signal Rn of one narrowband light.

The three image signals of the two wideband lights B and G and the one narrowband light Rn may be obtained by the color filter of the image pickup device 2A having the spectral characteristic shown in FIG. 15. Alternatively, it is also possible that three illumination lights (i.e., illumination lights of the two wideband lights B and G and the one narrowband light Rn) are generated using the rotating filter shown in FIG. 2 in the light source device and return lights of the three illumination lights are irradiated on a monochrome image pickup device to obtain the image signals.

Note that, in FIGS. 16 to 19, three image signals of two wideband lights and one narrowband light may be obtained by the color filter of the image pickup device 2A. Alternatively, the light source device may irradiate two or more illumination lights to thereby make a wavelength band of at least one illumination light (Rn) among the two or more illumination lights narrower than a wavelength band of the other illumination lights (B and G).

The spectral estimation section 101c estimates, according to the spectral estimation processing, the spectrally estimated image signals e1, e2, and e3 of the three narrowband lights from the image signals of the two wideband lights B and G and the image signal Rn of the one narrowband light. The spectrally estimated image signal e1 of the narrowband light near the wavelength of 600 nm, the spectrally estimated image signal e2 of the narrowband light near the wavelength of 630 nm, and the third estimated image signal e3 of the narrowband light near the wavelength of 540 nm are estimated from the image signals of the two wideband lights B and G and the image signal Rn of the one narrowband light having the wavelength bands shown in FIG. 15.

Note that at least the two spectrally estimated image signals e1 and e2 (here, the three spectral image signals e1, e2, and e3) may be obtained from an image signal of one wideband light (e.g., an image signal of the wideband light G) and an image signal of one narrowband light Rn according to the spectral estimation processing.

In FIG. 15, the one narrowband light Rn includes narrowband light near the wavelength of 600 nm. However, the one narrowband light Rn may include narrowband light near the wavelength of 630 nm. Further, the one narrowband light Rn may be narrowband light including neither narrowband light near the wavelength of 600 nm nor narrowband light near the wavelength of 630 nm indicated by an alternate long and short dash line in FIG. 15.

Figure 16:
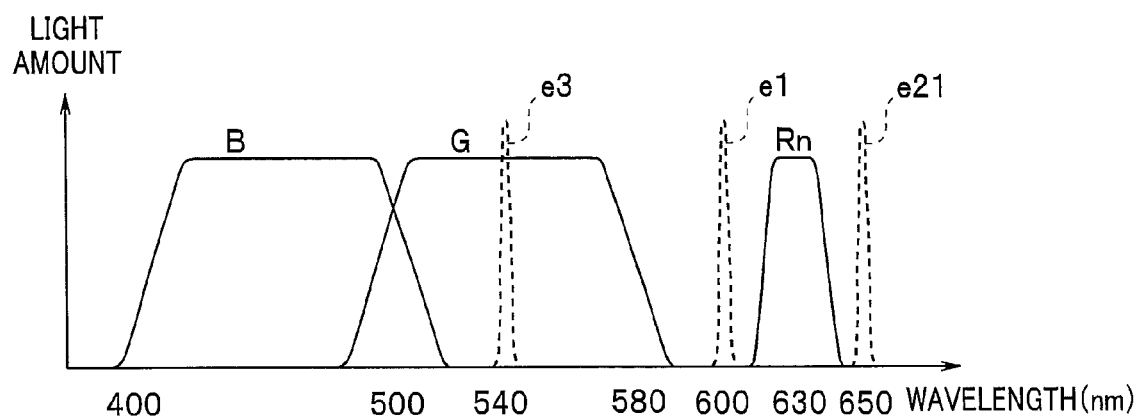
FIG. 16 is a diagram showing a spectral characteristic for explaining a case in which one narrowband light Rn does not include narrowband light of an estimated spectrally estimated image signal according to the second embodiment.

FIG. 16 is a diagram showing a spectral characteristic for explaining a case in which the one narrowband light Rn does not include narrowband light of an estimated spectrally estimated image signal. As shown in FIG. 16, here, the spectrally estimated image signal e1 of the narrowband light near the wavelength of 600 nm, a spectrally estimated image signal e21 of the narrowband light near the wavelength of 650 nm, and the spectrally estimated image signal e3 of the narrowband light near the wavelength of 540 nm are obtained from the image signals B and G of the two wideband lights and the image signal Rn of the one narrowband light according to the spectral estimation processing.

A second method is a method of estimating three spectrally estimated image signals from an image signal of one wideband light and image signals of two narrowband lights.

Figure 17:
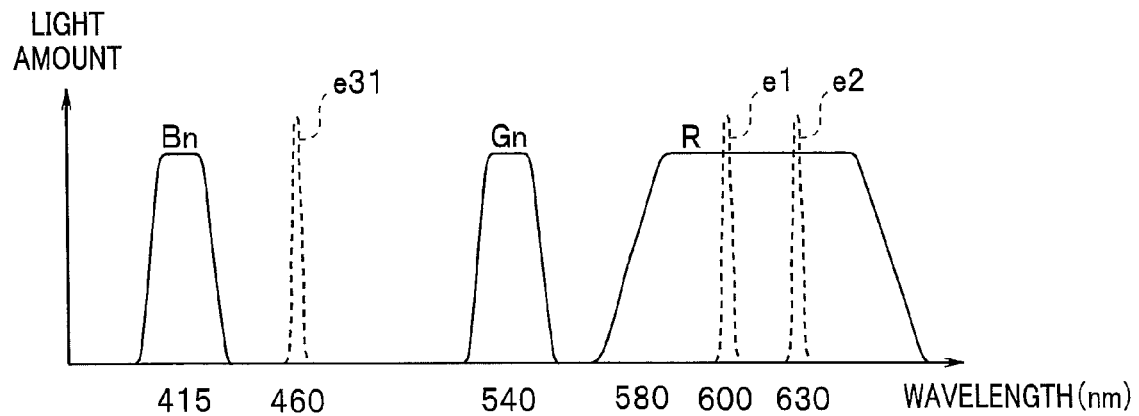
FIG. 17 is a diagram showing a spectral characteristic for explaining a case in which spectrally estimated image signals of three narrowband lights are estimated from an image signal of one wideband light and image signals of two narrowband lights according to the second embodiment.

FIG. 17 is a diagram showing a spectral characteristic for explaining a case in which spectrally estimated image signals of three narrowband lights are estimated from an image signal of one wideband light and image signals of two narrowband lights. As shown in FIG. 17, narrowband lights are used for B and G and wideband light is used for R. The spectral estimation section 101c estimates three spectrally estimated image signals e1, e2, and e31 from image signals Bn and Gn of two narrowband lights and an image signal of one wideband light R. The spectrally estimated image signal e31 is an image signal of narrowband light near a wavelength of 460 nm.

The three image signals of the two narrowband lights Bn and Gn and the one wideband light R may be obtained by the color filter of the image pickup device 2A having the spectral characteristic shown in FIG. 17. Alternatively, it is also possible that three illumination lights (i.e., illumination lights of the two narrowband lights Bn and Gn and the one narrowband light R) are generated using the rotating filter shown in FIG. 2 in the light source device and return lights of the three illumination lights are irradiated on a monochrome image pickup device to obtain the image signals.

The spectral estimation section 101c estimates, according to the spectral estimation processing, the spectrally estimated image signals e1, e2, and e31 of the three narrowband lights from the image signals Bn and Gn of the two narrowband lights and the image signal R of the one wideband light. The spectrally estimated image signal e1 of the narrowband light near the wavelength of 600 nm, the spectrally estimated image signal e2 of the narrowband light near the wavelength of 630 nm, and the third estimated image signal e31 of the narrowband light near the wavelength of 460 nm are estimated from the image signals Bn and Gn of the two narrowband lights and the image signal R of the one wideband light having the wavelength bands shown in FIG. 17.

Note that at least the two spectrally estimated image signals e1 and e2 (here, the three spectral image signals e1, e2, and e31) may be obtained from an image signal of one narrowband light (e.g., an image signal of the narrowband light Gn) and the image signal R of one wideband light according to the spectral estimation processing.

In FIG. 17, the one wideband light R includes the narrowband light near the wavelength of 600 nm and the narrowband light near the wavelength of 630 nm However, the one wideband light R may include only one of the narrowband lights, for example, the narrowband light near the wavelength of 630 nm.

Further, the one wideband light R may include neither the narrowband light near the wavelength of 600 nm nor the narrowband light near the wavelength of 630 nm.

A third method is a method of estimating three spectral image signals from image signals of three narrowband lights.

Figure 18:
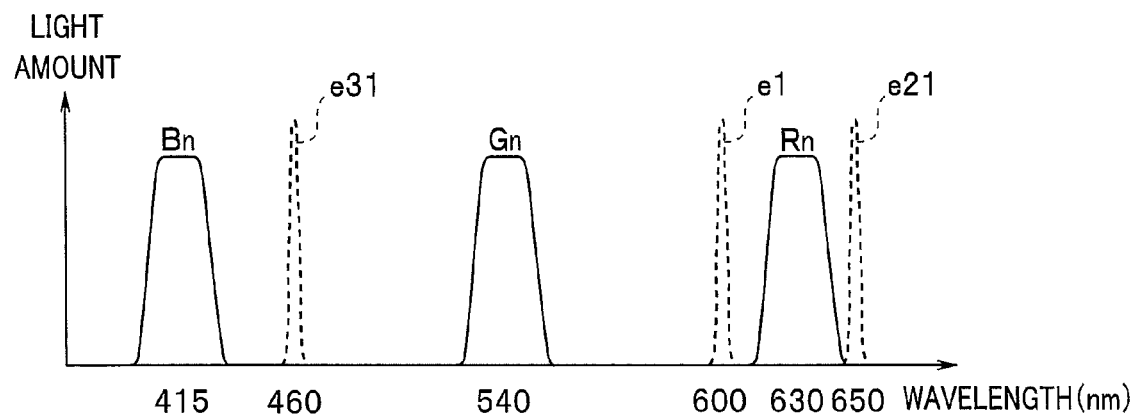
FIG. 18 is a diagram showing a spectral characteristic for explaining a case in which spectrally estimated image signals of three narrowband lights are estimated from image signals of three narrowband lights according to the second embodiment.

FIG. 18 is a diagram showing a spectral characteristic for explaining a case in which spectrally estimated image signals of three narrowband lights are estimated from image signals of three narrowband lights. As shown in FIG. 18, narrowband lights are used for B, G, and R. The spectral estimation section 101c estimates the three spectrally estimated image signals e1, e21, and e31 from the image signals B, G, and R of the three narrowband lights.

The three narrowband lights Bn, Gn, and Rn may be obtained by the color filter of the image pickup device 2A having the spectral characteristic shown in FIG. 18. Alternatively, it is also possible that three illumination lights (i.e., illumination lights of the three narrowband lights B, G, and R) are generated using the rotating filter shown in FIG. 2 in the light source device and return lights of the three illumination lights are irradiated on a monochrome image pickup device to obtain the narrowband lights Bn, Gn, and Rn.

The spectral estimation section 101c estimates, according to the spectral estimation processing, the three spectrally estimated image signals e1, e21, and e31 of the three narrowband lights from the image signals Bn, Gn, and Rn of the three narrowband lights. The spectrally estimated image signal e1 of the narrowband light near the wavelength of 600 nm, the spectrally estimated image signal e21 of the narrowband light near the wavelength of 650 nm, and the spectrally estimated image signal e31 of the narrowband light near the wavelength of 460 nm are estimated from the image signals Bn, Gn, and Rn of the three narrowband lights having the wavelength bands shown in FIG. 18.

Note that at least the two spectrally estimated image signals e1 and e21 (here, the three spectral image signals e1, e21, and e31) may be obtained from image signals of two narrowband lights, for example, the image signals Bn and Gn of the narrowband lights according to the spectral estimation processing.

At least one narrowband light may include wavelength of narrowband light of an estimated spectrally estimated image. For example, in FIG. 18, the narrowband light Rn does not include the narrowband light near the wavelength of 600 nm and the narrowband light near the wavelength of 630 nm. However, the narrowband light Rn may include only one of the narrowband lights, for example, the narrowband light near the wavelength of 600 nm. Further, in FIG. 18, the narrowband light Bn does not include the narrowband light near the wavelength of 460 nm. However, the narrowband light Bn may include the narrowband light near the wavelength of 460 nm.

A fourth method is a method of estimating three spectrally estimated image signals from image signals of four narrowband lights.

Figure 19:
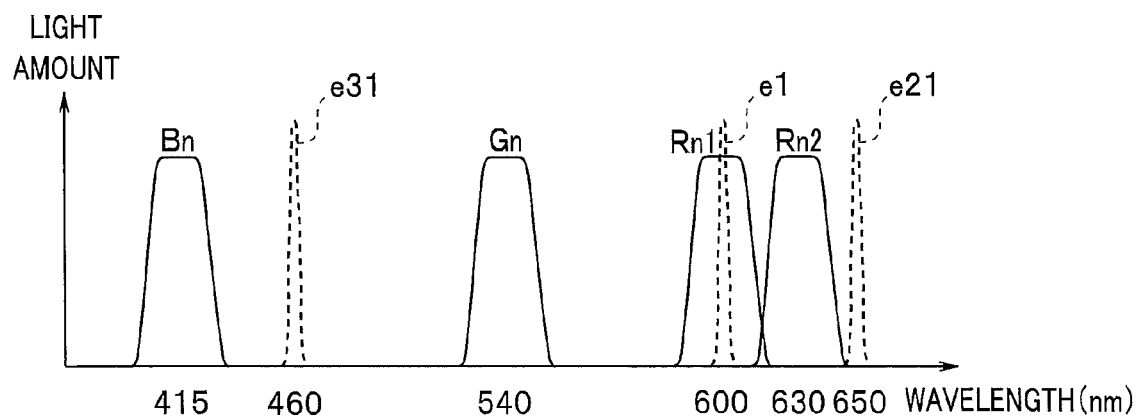
FIG. 19 is a diagram showing a spectral characteristic for explaining a case in which spectral image signals of three narrowband lights are estimated from image signals of four narrowband lights according to the second embodiment.

FIG. 19 is a diagram showing a spectral characteristic for explaining a case in which spectral image signals of three narrowband lights are estimated from image signals of four narrowband lights. As shown in FIG. 19, narrowband lights are used for Bn, Gn, and Rn. However, two narrowband lights are used for Rn. The spectral estimation section 101c estimates the three spectrally estimated image signals e1, e21, and e31 from image signals of four narrowband lights Bn, Gn, and Rn.

Four narrowband lights Bn, Gn, Rn1, and Rn2 may be obtained by the color filter of the image pickup device 2A having the spectral characteristic shown in FIG. 19. Alternatively, it is also possible that four illumination lights (i.e., illumination lights of the four narrowband lights Bn, Gn, Rn1, and Rn2) are generated using the rotating filter shown in FIG. 2 in the light source device and return lights of the illumination lights are irradiated on a monochrome image pickup device to obtain the four narrowband lights Bn, Gn, Rn1, and Rn2.

The spectral estimation section 101c estimates, according to the spectral estimation processing, the spectrally estimated image signals e1, e21, and e31 of the three narrowband lights from image signals of the four narrowband lights Bn, Gn, Rn1, and Rn2. The spectrally estimated image signal e1 of the narrowband light near the wavelength of 600 nm, the spectrally estimated image signal e21 of the narrowband light near the wavelength of 650 nm, and the spectrally estimated image signal e31 of the narrowband light near the wavelength of 460 nm are estimated from the image signals Bn, Gn, Rn1, and Rn2 of the four narrowband lights having the wavelength bands shown in FIG. 19.

Spectral estimation accuracy is improved when three spectrally estimated image signals are estimated from image signals of four or more narrowband lights compared with when three spectrally estimated image signals are estimated from image signals of three narrowband lights. Therefore, the at least two spectrally estimated image signals e1 and e21 (here, the three spectrally estimated image signals e1, e21, and e31) may be obtained from image signals of four or more narrowband lights, for example, image signals of the narrowband lights Bn, Gn, Rn1, and Rn2 according to the spectral estimation processing.

Two or more of a plurality of narrowband lights may include wavelength of narrowband light of an estimated spectrally estimated image. For example, in FIG. 19, the narrowband light Rn does not include the narrowband light near the wavelength of 650 nm. However, the narrowband light Rn may include the narrowband light near the wavelength of 650 nm. Further, in FIG. 19, the narrowband light Bn does not include the narrowband light near the wavelength of 460 nm. However, the narrowband light Bn may include the narrowband light near the wavelength of 460 nm.

Figure 20:
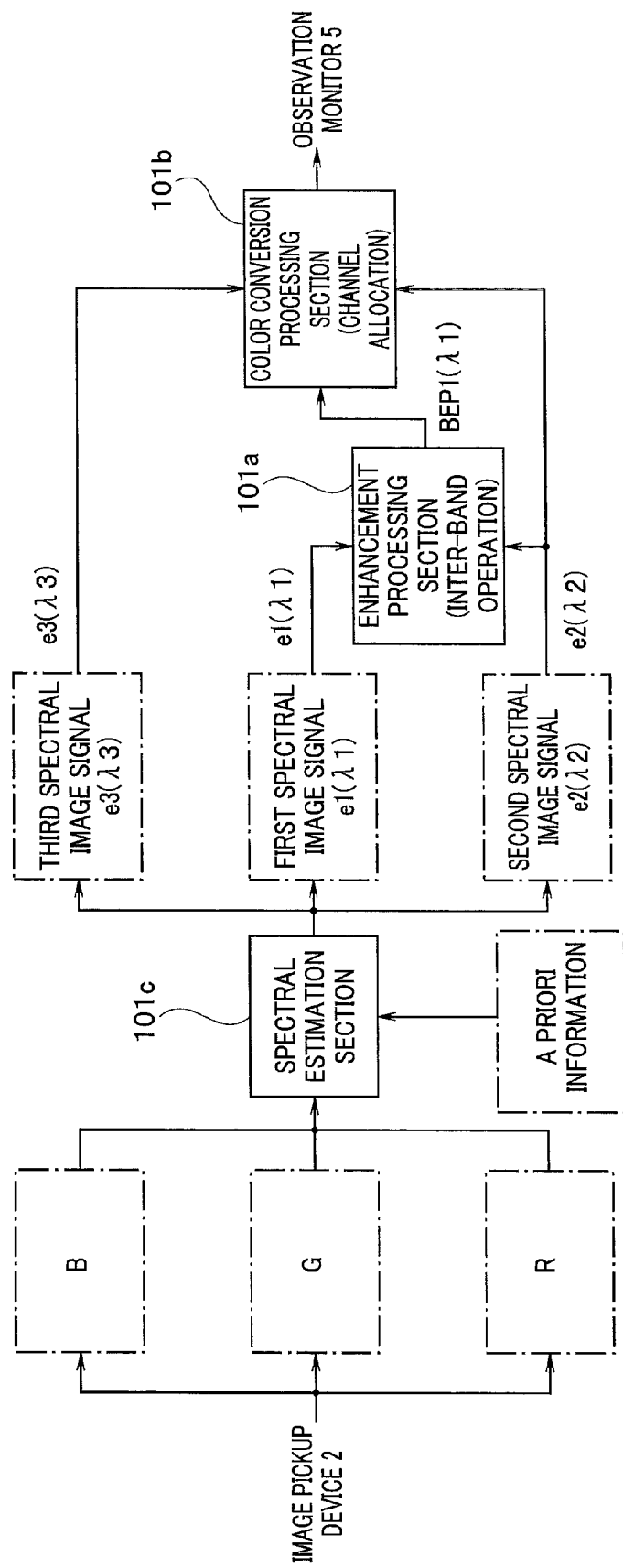
FIG. 20 is a diagram for explaining a flow of processing for an image obtained from the image pickup device 2 in an image processing section 101A according to the second embodiment.

FIG. 20 is a diagram for explaining a flow of processing for an image obtained from the image pickup device 2 in the image processing section 101A in the present embodiment.

As shown in FIG. 20, three images, i.e., first to third image signals P1, P2, and P3 are inputted to the spectral estimation section 101c from the image pickup device 2. The spectral estimation section 101c estimates and generates the three spectrally estimated image signals e1, e2, and e3 from inputted two or three image signals.

The enhancement processing section 101a applies the enhancement processing by the inter-band operation to the two spectral image signals e1 and e2 among the three spectral image signals e1, e2, and e3 obtained by the spectral estimation section 101c. The color conversion processing section 101b applies the color conversion processing by the channel allocation to the second spectrally estimated image signal e2, the third spectrally estimated image signal e3, and the enhanced corrected image signal BEP1 (λ1) obtained by the enhancement processing and outputs the image signals to the observation monitor 5.

Note that, in the second embodiment, the color filter of the RGB system is explained as an example of the color filter provided on the surface of the image pickup device. However, the color filter may be a color filter of a complementary color system.

Wavelength of the second spectrally estimated signal e2 or e21 shown in FIGS. 14 to 19 may be light in a wavelength band longer than the minimum value ACmin (here, an absorption coefficient at wavelength of 730 nm) of the absorption characteristic of hemoglobin shown in FIG. 4. That is, the wavelength of the second spectrally estimated signal e2 or e21 is a wavelength band in which an absorption coefficient is lower than the absorption coefficient of the wavelength of the first spectrally estimated signal e1 and a scattering characteristic of a living body tissue is suppressed more than the scattering characteristic of the wavelength of the first spectrally estimated signal e1. For example, even when 740 nm, 770 nm, 805 nm, 810 nm, 850 nm, 870 nm, 880 nm, 910 nm, 940 nm, 1020 nm, and 1300 nm are used, it is possible to obtain effects equivalent to the effects explained above (e.g., when the wavelength of the second spectrally estimated signal e2 or e21 is set to any one of the wavelengths of 740 nm to 1300 nm, the wavelength of the first spectrally estimated signal e1 is set to any wavelength equal to or higher than 576 nm and at least equal to or lower than 630 nm).

In the endoscope in the present embodiment, by performing the enhancement processing explained above, a relatively thick blood vessel present in a relatively deep part of the living body mucosa is highlighted and displayed on the screen of the observation monitor 5. Therefore, the surgeon can perform desired treatment such as ESD while looking at and checking the relatively thick blood vessel as well.

The endoscope apparatus 1A explained above can also display a blood vessel present in a portion close to the surface layer of the living body mucosa using the third spectrally estimated image signal e3. Therefore, the endoscope apparatus 1A can also be used for performing, from a state of capillaries, for example, a degree of a concentration degree or a dispersion degree of the capillaries, a diagnosis of a living body tissue, for example, a presence diagnosis of cancer or a range diagnosis for specifying a range of cancer and a discrimination diagnosis for determining whether a diseased part is benign or malignant. Further, for example, a penetration depth diagnosis with consciousness directed to a blood vessel of a deeper part can also be performed.

Note that the blood vessel may be subjected to the color conversion processing and displayed on the observation monitor 5 further using fourth and fifth images obtained by spectrally estimating in addition to the third spectrally estimated image signal e3.

As explained above, according to the present embodiment, it is possible to provide an endoscope apparatus that can clearly display a blood vessel in a mucosa deep part without performing complicated work of drug administration.

Third Embodiment

In the first embodiment, at least one narrowband light is actually irradiated on a living body tissue as illumination light and the enhancement processing explained above is applied to an image of return light of the illumination light. In the second embodiment, three narrowband lights are not actually irradiated on a living body tissue, image information of return lights of respective narrowband lights is obtained by so-called spectral estimation, and the enhancement processing explained above is applied to spectrally estimated image signals having respective wavelengths obtained by the spectral estimation. However, in the third embodiment, the enhancement processing explained above is applied to an image signal of return light of actual illumination light of narrowband light and a spectrally estimated image signal obtained by the spectral estimation.

Figure 21:
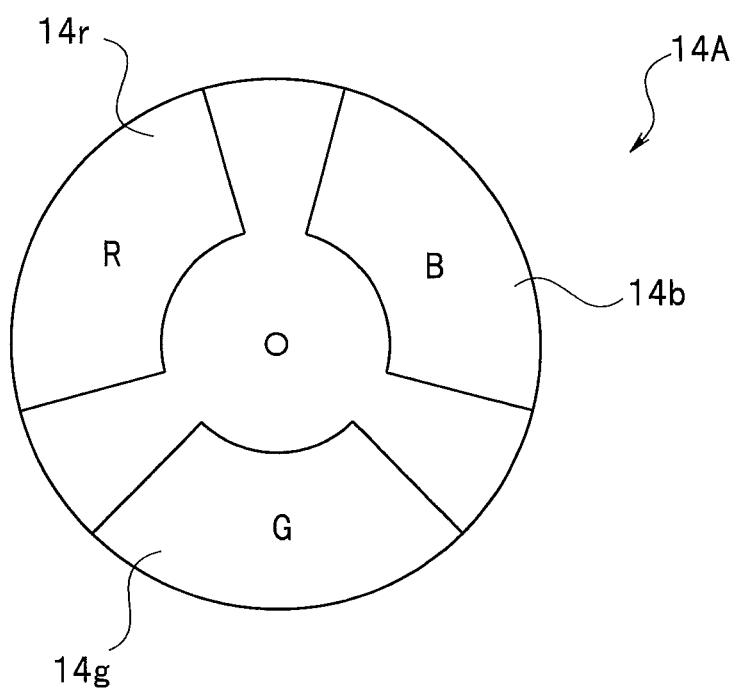
FIG. 21 is a diagram showing a configuration of a rotating filter 14A according to a third embodiment.

A configuration of an endoscope apparatus 1B in the present embodiment is the same as the configuration of the endoscope apparatus 1 shown in FIG. 1. However, a configuration of a rotating filter 14A in the present embodiment is different. FIG. 21 is a diagram showing the configuration of the rotating filter 14A in the present embodiment. As shown in FIG. 21, the rotating filter 14A includes only filter sections of RGB configuring a filter set for outputting frame-sequential light having a spectral characteristic for normal light observation. Return lights of frame-sequential BGR lights are received by the monochrome image pickup device 2.

Figure 22:
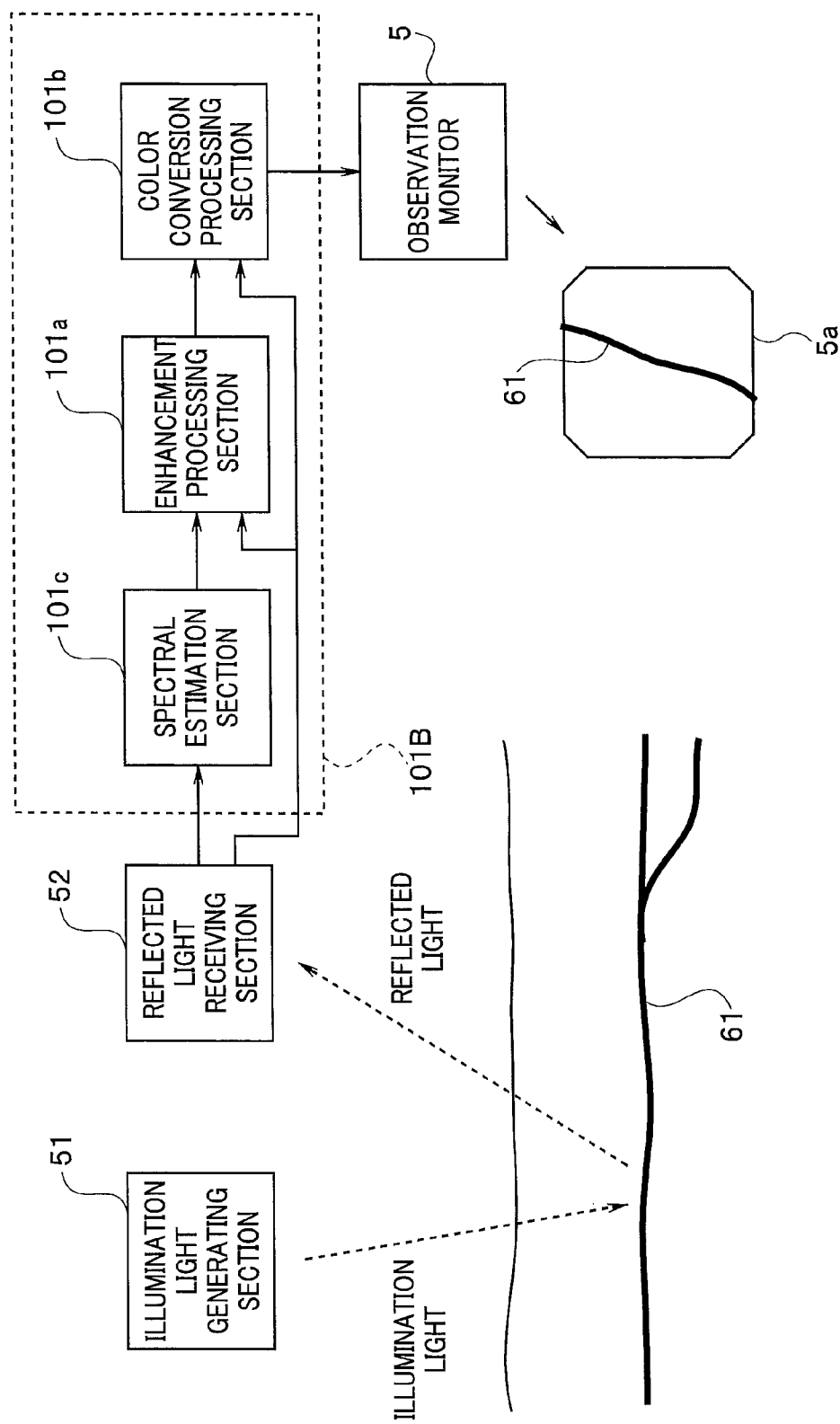
FIG. 22 is a diagram for explaining a flow of overall processing in a special light observation mode according to the third embodiment.

FIG. 22 is a diagram for explaining a flow of overall processing in a special light observation mode according to the present embodiment. In FIG. 22, components same as the components shown in FIG. 13 are denoted by the same reference numerals and signs and explanation of the components is omitted. An image processing section 101B includes the enhancement processing section 101a, the color conversion processing section 101b, and the spectral estimation section 101c. The spectral estimation section 101c generates at least one spectrally estimated image signal e from two or three image signals among RGB. The enhancement processing by the inter-band operation is performed between one image signal among RGB and the spectrally estimated image signal.

Here, more specifically, the first spectrally estimated image signal e1 near a wavelength of 600 nm and the third spectrally estimated image signal e3 near a wavelength of 540 nm are estimated from three (or two) image signals among RGB according to the spectral estimation processing and outputted to the enhancement processing section 101a.

Figure 23:
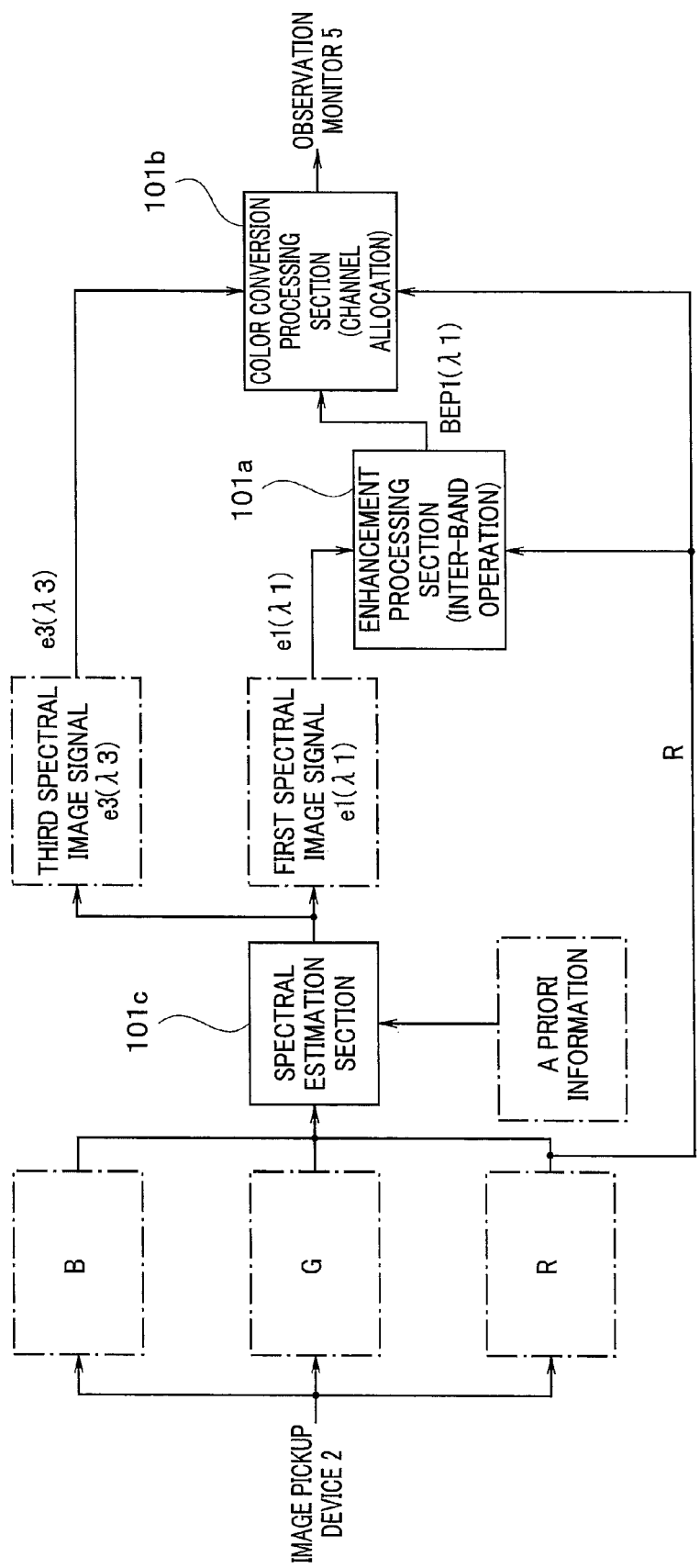
FIG. 23 is a diagram for explaining a flow of processing for an image obtained from the image pickup device 2 in an image processing section 101B according to the third embodiment.

FIG. 23 is a diagram for explaining a flow of processing for an image obtained from the image pickup device 2 in the image processing section 101B according to the present embodiment.

As shown in FIG. 23, three images, i.e., first to third image signals B, G, and R are inputted to the spectral estimation section 101c from the image pickup device 2. The spectral estimation section 101c estimates and generates the two spectrally estimated image signals e1 and e3 from the inputted two or three images.

The enhancement processing section 101a applies the enhancement processing by the inter-band operation to the image signal R and the spectral image signal e1 of the two spectrally estimated image signals e1 and e3 obtained by the spectral estimation section 101c. The color conversion processing section 101b applies the color conversion processing by the channel allocation to the spectrally estimated image signal e3, the enhanced corrected image signal BEP1 (λ1) obtained by the enhancement processing, and the image signal R and outputs the image signals to the observation monitor 5.

Note that processing in the enhancement processing section 101a and the color conversion processing section 101b is the same as the processing in the first embodiment.

Figure 24:
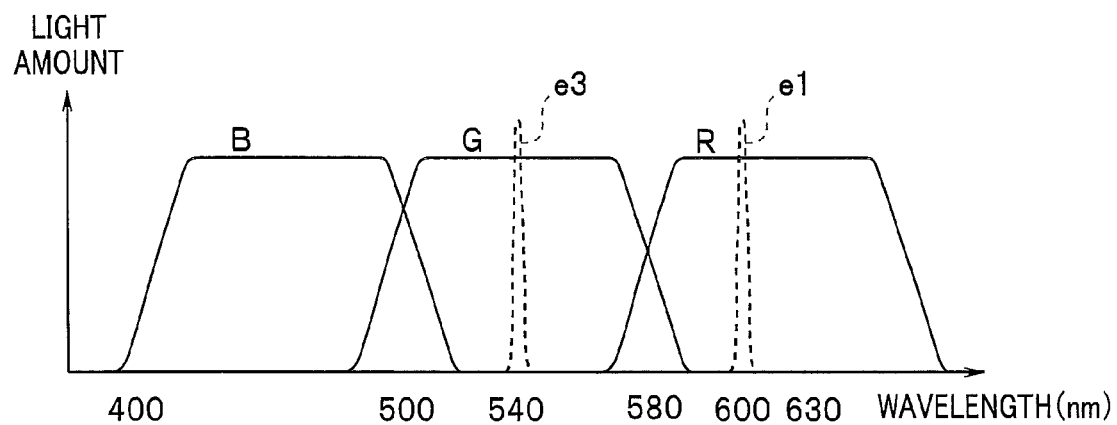
FIG. 24 is a diagram showing a spectral characteristic for explaining a case in which spectrally estimated image signals e1 and e3 of two narrowband lights are estimated from image signals B, G, and R of three (or two) wideband lights according to the third embodiment.

FIG. 24 is a diagram showing a spectral characteristic for explaining a case in which the spectrally estimated image signals e1 and e3 of two narrowband lights are estimated from the image signals B, G, and R of three (or two) wideband lights.

The image signal R based on real light of the wideband light R from the reflected light receiving section 52 and the spectrally estimated image signal e1 near the wavelength of 600 nm outputted from the spectral estimation section 101c are inputted to the enhancement processing section 101a. The spectral image signal e1 is a spectrally estimated image signal of one narrowband light within the wavelength band R from the maximum value ACmax to the minimum value ACmin in FIG. 4.

The enhancement processing section 101a performs the enhancement processing by the inter-band operation explained above between the inputted image signal R and spectrally estimated image signal e1 and outputs the enhanced corrected image signal BEP1 ($\lambda$1) subjected to the enhancement processing to the color conversion processing section 101b.

That is, the spectral estimation section 101c spectrally estimates and generates at least one spectral image signal e1 according to signal processing on the basis of at least two image pickup signals of return light from a subject. The enhancement processing section 101a applies processing for enhancing the spectral image signal e1 to the spectral image signal e1 and an image signal of return light picked up by the image pickup device 2, which is image pickup means or an image pickup section, and generates and outputs the enhanced image signal.

The spectrally estimated image signal e3 outputted from the spectral estimation section 101c, the enhanced corrected image signal BEP1 ($\lambda$1) subjected to the enhancement processing by the enhancement processing section 101a, and the real image signal R are inputted to the color conversion processing section 101b. As explained above, processing in the color conversion processing section 101b is the same as the processing explained in the first embodiment.

Note that, the three wideband lights B, G, and R in FIG. 23 may be obtained by the color filter of the image pickup device 2A. That is, the three wideband lights B, G, and R may be obtained using the light source device 4A and the color filter of the image pickup device 2A explained in the second embodiment.

Therefore, effects same as the effects of the endoscope apparatuses 1 and 1A explained above can be obtained by the endoscope apparatus 1B in the present embodiment.

In the spectral image signal e1 spectrally estimated by the signal processing and the image signal of the return light picked up by the image pickup section, wavelength of a signal having wavelength information on a longer wavelength side may be light in a wavelength band longer than the minimum value ACmin (here, an absorption coefficient at wavelength of 730 nm) of the absorption characteristic of hemoglobin in FIG. 4. That is, the wavelength of the signal having the wavelength information on the longer wavelength side is a wavelength band in which an absorption coefficient is lower than the absorption coefficient of the wavelength of the other signal and a scattering characteristic of a living body tissue is suppressed more than the scattering characteristic of the wavelength of the other signal. For example, even when 740 nm, 770 nm, 805 nm, 810 nm, 850 nm, 870 nm, 880 nm, 910 nm, 940 nm, 1020 nm, and 1300 nm are used, it is possible to obtain effects equivalent to the effects explained above (e.g., when the wavelength of the signal having the wavelength information on the longer wavelength side is set to any one of the wavelengths of 740 nm to 1300 nm, the wavelength of the other signal is set to any wavelength equal to or higher than 576 nm and at least equal to or lower than 630 nm).

Next, modifications of a real image signal and a spectrally estimated image signal used in the inter-band operation are explained. In the example explained above, the inter-band operation is performed between the image signal of the wideband light R and the spectrally estimated image signal e1. However, the inter-band operation is not limited to such a method. Methods of modifications explained below may be used.

(Modification 1)

A first method is a method of performing the inter-band operation between the image signal Rn of one narrowband light and the spectrally estimated image signal e2.

Figure 25:
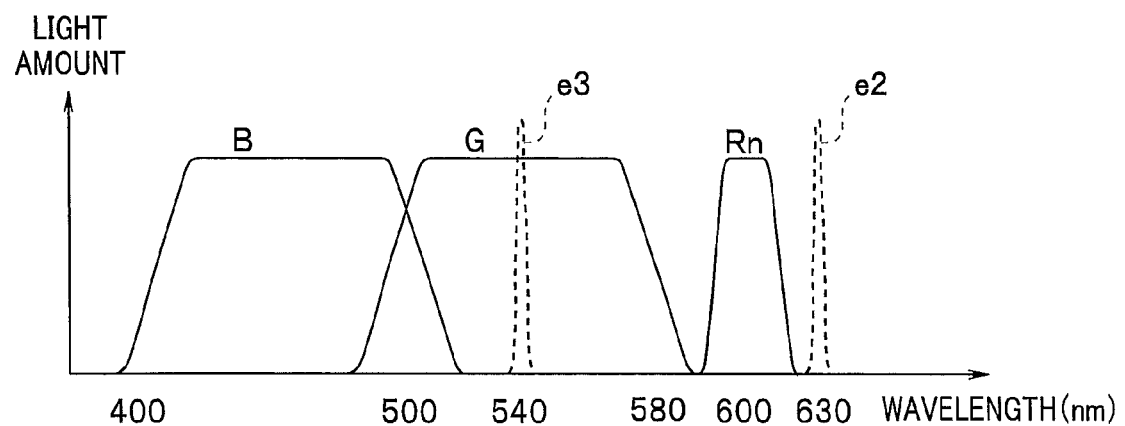
FIG. 25 is a diagram showing a spectral characteristic for explaining a case in which an inter-band operation is performed between an image signal Rn of narrowband light near a wavelength of 600 nm ($\lambda 1$) and one spectrally estimated image signal e2 according to the third embodiment.

FIG. 25 is a diagram showing a spectral characteristic for explaining a case in which the inter-band operation is performed between the image signal Rn of the narrowband light near the wavelength of 600 nm ($\lambda$1) and the one spectrally estimated image signal e2. As shown in FIG. 25, one narrowband light is the narrowband light Rn near the wavelength of 600 nm ($\lambda$1) and is a real image signal. One spectrally estimated image signal is the spectrally estimated image signal e2 of the narrowband light near the wavelength of 630 nm estimated by the spectral estimation from three (or two) out of the image signals B and G of two wideband lights and the image signal Rn of one narrowband light. The inter-band operation is performed between the image signal Rn of the narrowband light and the spectral image signal e2. In the case of FIG. 25, since the real image signal of the narrowband light is used, a thick blood vessel in a deep part is enhanced and displayed more than when the real image signal in the wideband is used as shown in FIG. 24.

Figure 26:
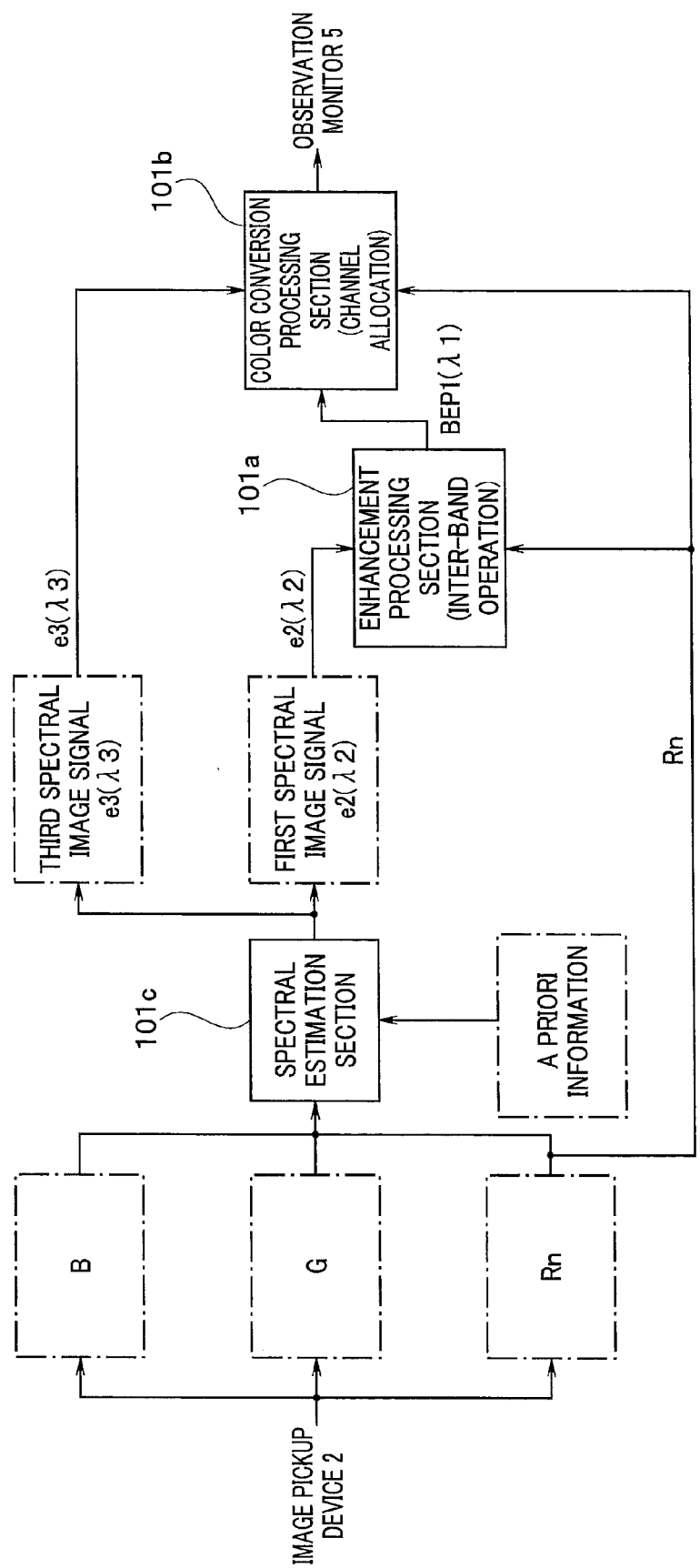
FIG. 26 is a diagram for explaining a flow of processing for an image obtained from the image pickup device 2 in the image processing section 101B according to a modification 1 of the third embodiment.

FIG. 26 is a diagram for explaining a flow of processing for an image obtained from the image pickup device 2 in the image processing section 101B in the modification 1 of the present embodiment.

As shown in FIG. 26, three images, i.e., the first to third image signals B, G, and Rn are inputted to the spectral estimation section 101c from the image pickup device 2. The spectral estimation section 101c estimates and generates the two spectrally estimated image signals e2 and e3 from the inputted three (or two) image signals.

The enhancement processing section 101a applies the enhancement processing by the inter-band operation to the image signal Rn and the spectral image signal e2 of the two spectrally estimated image signals e2 and e3 obtained by the spectral estimation section 101c. The color conversion processing section 101b applies the color conversion processing by the channel allocation to the spectrally estimated image signal e3, the enhanced corrected image signal BEP1 ($\lambda$1) obtained by the enhancement processing, and the image signal Rn and outputs the image signals to the observation monitor 5.

Figure 27:
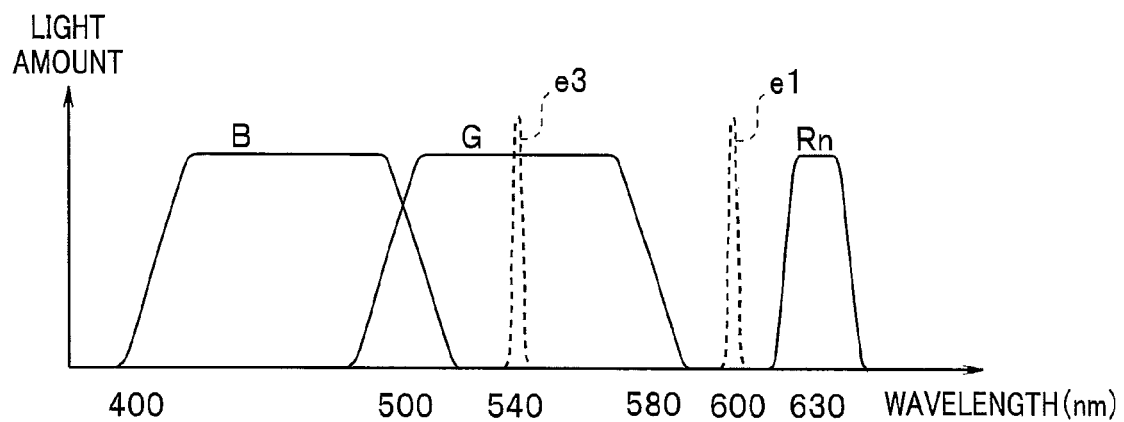
FIG. 27 is a diagram showing a spectral characteristic for explaining a case in which an inter-band operation is performed between an image signal Rn of narrowband light near a wavelength of 630 nm ($\lambda 2$) and one spectrally estimated image signal e1 according to the modification 1 of the third embodiment.

Note that the inter-band operation may be performed between the narrowband light Rn near the wavelength of 630 nm ($\lambda$2) and the one spectrally estimated image signal e1. FIG. 27 is a diagram showing a spectral characteristic for explaining a case in which the inter-band operation is performed between the image signal Rn of the narrowband light near the wavelength of 630 nm ($\lambda$2) and the one spectrally estimated image signal e1. An image signal in processing for an image obtained from the image pickup device 2 in the image processing section 101B in this case is an image signal indicated by parentheses in FIG. 26. That is, the enhancement processing section 101a outputs the enhanced corrected image signal BEP1 ($\lambda$1). The color conversion processing section 101*b* applies the color conversion processing by the channel allocation to the enhanced corrected image signal BEP1 ($\lambda$1) and the image signal Rn.

The three image signals of the two wideband lights B and G and the one narrowband light Rn can be obtained by generating three illumination lights (i.e., illumination lights of the two wideband lights B and G and the one narrowband light R) using the rotating filter shown in FIG. 2, which has the spectral characteristic shown in FIG. 25 or 27, in the light source device and irradiating return lights of three illumination lights on a monochrome image pickup device.

Note that the three image signals of the two wideband lights B and G and the one narrowband light R may be obtained by the color filter of the image pickup device 2A having the spectral characteristic shown in FIG. 25 or 27.

As explained above, the spectral estimation section 101*c* estimates the two spectrally estimated image signals e1 (or e2) and e3 from the image signals B and G of two wideband lights and the image signal Rn of one narrowband light according to the spectral estimation processing. In the case of FIG. 25 or 27, the spectrally estimated image signal e2 of the narrowband light near the wavelength of 630 nm (or the spectrally estimated image signal e1 of the narrowband light near the wavelength of 600 nm) and the spectrally estimated image signal e3 of the narrowband light near the wavelength of 540 nm are estimated from the image signals of the two wideband lights B and G and the image signal of the one narrowband light Rn.

The color conversion processing section 101*b* applies the color conversion processing by the channel allocation to the spectrally estimated image signal e3, an enhanced corrected image signal BEP2 ($\lambda$2) (or the enhanced corrected image signal BEP1 ($\lambda$1)) obtained by the enhancement processing, and the image signal Rn and outputs the image signals to the observation monitor 5.

At least the two spectrally estimated image signals e2 (or e1) and e3 may be obtained from the image signals B and G of two wideband lights according to the spectral estimation processing. Alternatively, at least the two spectrally estimated image signals e2 (or e1) and e3 may be obtained from the one wideband light B (or G) and the image signal Rn of one narrowband light according to the spectral estimation processing.

(Modification 2)

Figure 28:
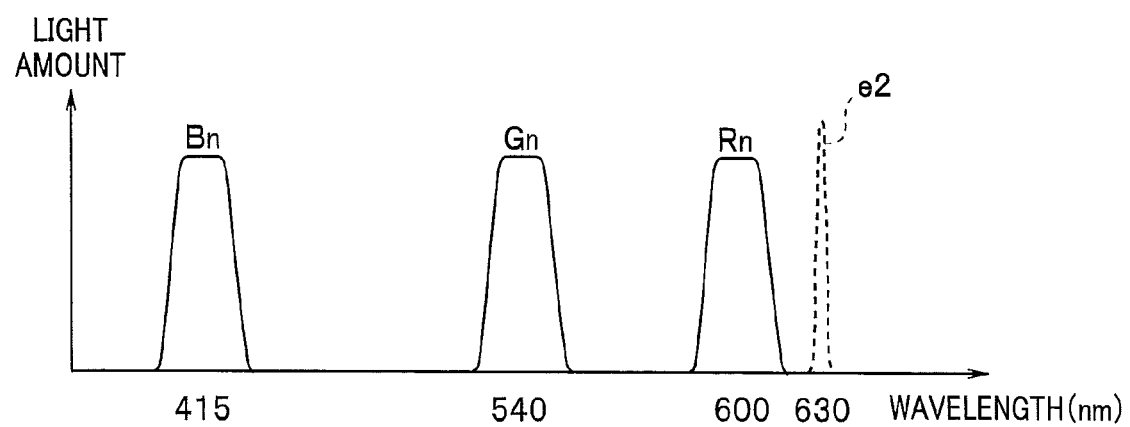
FIG. 28 is a diagram showing a spectral characteristic for explaining a case in which one spectrally estimated image signal e2 is estimated from image signals Bn, Gn, Rn of three narrowband lights according to a modification 2 of the third embodiment.

Further, the one spectral image signal e2 may be estimated from the image signals Bn, Gn, and Rn of three narrowband lights and the inter-band operation may be performed between the image signal Rn of one narrowband light and the one spectrally estimated image signal e2. FIG. 28 is a diagram showing a spectral characteristic for explaining a case in which the one spectrally estimated image signal e2 is estimated from the image signals Bn, Gn, and Rn of three narrowband lights.

As shown in FIG. 28, the three narrowband lights are narrowband light Rn near a wavelength of 600 nm, narrowband light Gn near a wavelength of 540 nm, and narrowband light Bn near a wavelength of 415 nm and are real image signals. One spectral image signal is the spectrally estimated image signal e2 of the narrowband light near the wavelength of 630 nm. The inter-band operation is performed between image signals of the narrowband light Rn near the wavelength of 600 nm and the spectrally estimated image signal e2 of the narrowband light near the wavelength of 630 nm.

Note that it is also possible that, for example, lighting of the narrowband light Gn near the wavelength of 540 nm and the narrowband light Rn near the wavelength of 600 nm is irradiated as the two narrowband lights, the spectrally estimated image signal e2 of the narrowband light near the wavelength of 630 nm is spectrally estimated from obtained image signals of the two image signals Gn and Rn, and the inter-band operation is performed between a real image signal of the narrowband light Rn near the wavelength of 600 nm and the spectrally estimated image signal e2.

Figure 29:
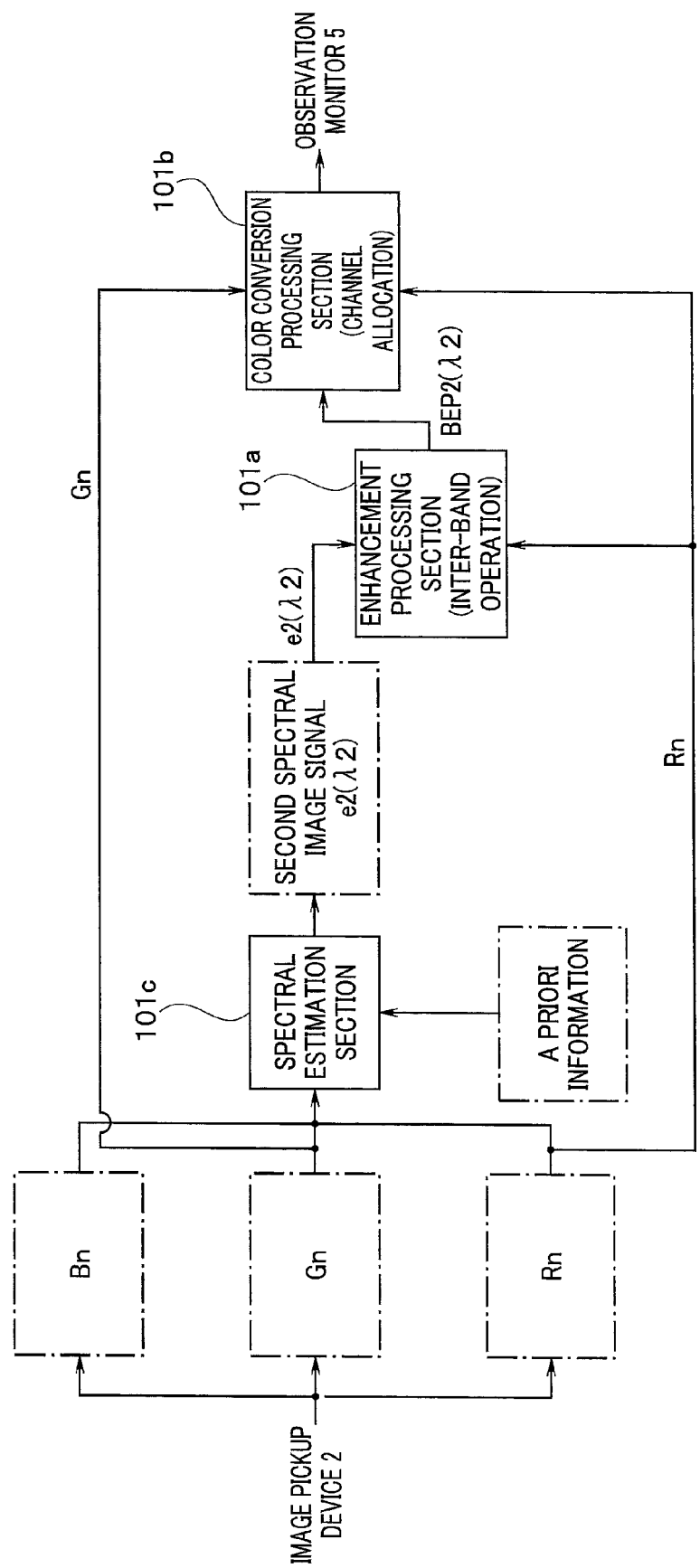
FIG. 29 is a diagram for explaining a flow of processing for an image obtained from the image pickup device 2 in the image processing section 101B according to the modification 2 of the third embodiment.

FIG. 29 is a diagram for explaining a flow of processing for an image obtained from the image pickup device 2 in the image processing section 101B in the modification 2 of the present embodiment.

As shown in FIG. 29, three image signals, i.e., the first to third image signals Bn, Gn, and Rn are inputted to the spectral estimation section 101*c* from the image pickup device 2. The spectral estimation section 101*c* estimates and generates the two spectrally estimated image signals e2 from the inputted three (or two) image signals.

The enhancement processing section 101*a* applies the enhancement processing by the inter-band operation to the spectral estimation image signal e2 obtained by the spectral estimation section 101*c* and the narrowband light Rn. The color conversion processing section 101*b* applies the color conversion processing by the channel allocation to the two narrowband lights Rn and Gn and the enhanced corrected image signal BEP2 ($\lambda$2) obtained by the enhancement processing and outputs the narrowband lights Rn and Gn and the enhanced corrected image signal BEP2 ($\lambda$2) to the observation monitor 5.

Figure 30:
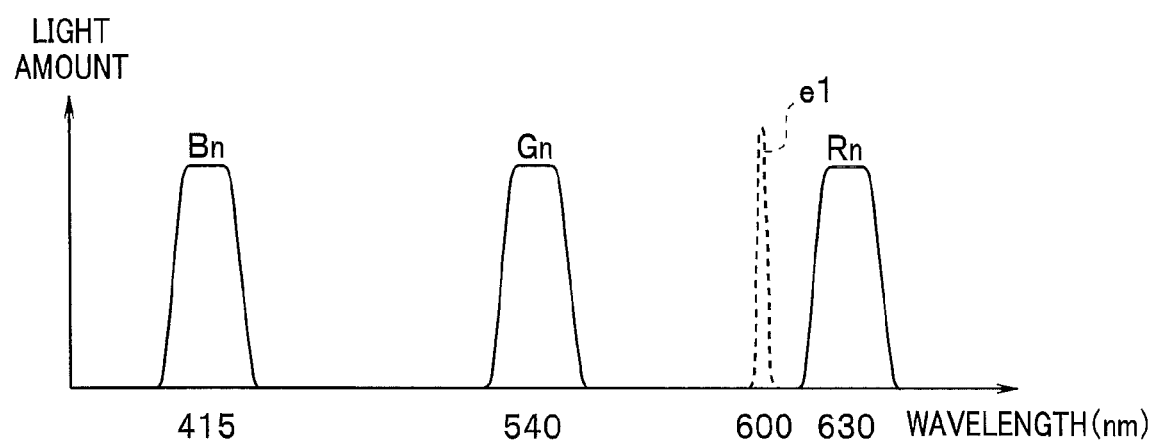
FIG. 30 is a diagram showing a spectral characteristic for explaining a case in which an inter-band operation is performed between an image signal Rn of narrowband light near a wavelength of 630 nm ($\lambda 2$) and one spectrally estimated image signal e1 according to the modification 2 of the third embodiment.

Note that the spectrally estimated image signal e1 near the wavelength of 600 nm may be obtained according to the spectral estimation using the narrowband light Rn near the wavelength 630 nm instead of the narrowband light Rn near the wavelength 600 nm. The inter-band operation may be performed between image signals of the narrowband light R near the wavelength of 630 nm and the spectrally estimated image signal e1 near the wavelength of 600 nm. FIG. 30 is a diagram showing a spectral characteristic for explaining a case in which the inter-band operation is performed between the image signal Rn of the narrowband light near the wavelength of 630 nm ($\lambda$2) and the one spectrally estimated image signal e1. An image signal in processing for an image obtained from the image pickup device 2 in the image processing section 101B in this case is an image signal indicated by parentheses in FIG. 29. That is, the enhancement processing section 101*a* outputs the enhanced corrected image signal BEP1 ($\lambda$1). The color conversion processing section 101*b* applies the color conversion processing by the channel allocation to the enhanced corrected image signal BEP1 ($\lambda$1) and the image signal Rn.

Furthermore, the image signals Bn, Gn, and Rn of three narrowband lights may be obtained by the color filter of the image pickup device 2A having the spectral characteristic shown in FIG. 28 or 30.

Note that, in the color conversion processing section 101*b*, the color conversion processing may be performed from four image signals including the image signal Bn of narrowband light in addition to the image signals of the two narrowband lights Gn and Rn and the spectrally estimated image signals e1 (or e2). Alternatively, fourth and fifth spectrally estimated image signals obtained by performing the spectral estimation may be subjected to the color conversion processing in addition to the image signal Bn of narrowband light or separately from the image signal Bn of narrowband light and displayed on the observation monitor 5.

Note that, in the third embodiment and the respective modifications, when the color filter provided on the surface of the image pickup device are used, the color filers of the RGB system are explained as an example. However, the color filter may be a color filter of the complementary color system.

In the endoscope in the present embodiment, by performing the enhancement processing explained above, a relatively thick blood vessel present in a relatively deep part of the living body mucosa is highlighted and displayed on the screen of the observation monitor 5. Therefore, the surgeon can perform desired treatment such as ESD while looking at and checking the relatively thick blood vessel as well.

The endoscope apparatus 1A explained above can also display a blood vessel present in a portion close to the surface layer of the living body mucosa using the spectrally estimated image signal e3 or the narrowband light Gn corresponding to the third narrowband light NL3. Therefore, the endoscope apparatus 1A can also be used for performing, from a state of capillaries, for example, a degree of a concentration degree or a dispersion degree of the capillaries, a diagnosis of a living body tissue, for example, a presence diagnosis of cancer or a range diagnosis for specifying a range of cancer and a discrimination diagnosis for determining whether a diseased part is benign or malignant. Further, for example, a penetration depth diagnosis with consciousness directed to a blood vessel of a deeper part can also be performed.

As explained above, according to the present embodiment, it is possible to provide an endoscope apparatus that can clearly display a blood vessel in a mucosa deep part without performing complicated work of drug administration.

(Modifications Common to the Respective Embodiments)
(Modification 1)

In the three embodiments and the respective modifications of the embodiments explained above, the light absorption characteristic of the venous blood is explained as an example and the two narrowband lights are selected on the basis of the characteristic. However, the at least two narrowband lights explained above may be selected on the basis of a light absorption characteristic of arterial blood or a light absorption characteristic of blood obtained by combining both of the venous blood and the arterial blood.

(Modification 2)

In the endoscope apparatuses in the respective embodiments and the respective modifications (including the modifications of the respective embodiments) explained above, light near the wavelength of 600 nm and light near the wavelength of 630 nm are used as the wavelengths of the first narrowband light NL1 and the second narrowband NL2. However, the wavelengths of the first narrowband light NL1 and the second narrowband light NL2 are preferably respectively wavelength in a range of wavelength of 580 to 620 nm and narrowband light having a distribution in a range of predetermined width and wavelength in a range of wavelength of 610 to 730 nm and narrowband light having a distribution in a range of predetermined width and more preferably respectively wavelength in a range of wavelength of 585 to 615 nm and narrowband light having a distribution in a range of predetermined width and wavelength in a range of wavelength of 620 to 640 nm and narrowband light having a distribution in a range of predetermined width.

Therefore, the wavelengths of the first narrowband light NL1 and the second narrowband light NL2 are not respectively limited to the light near the wavelength of 600 nm and the light near the wavelength of 630 nm and may be light having any wavelength as long as the light has the absorption characteristic explained above between the minimum value and the minimum value of the absorption characteristic. For example, as the wavelengths of the first narrowband light NL1 and the second narrowband light NL2, light near the wavelength of 610 nm and light near the wavelength of 645 nm or light near the wavelength of 630 nm or light near the wavelength of 660 nm may be respectively used.

(Modification 3)

In the endoscope apparatuses in the respective embodiments and the respective modifications (including the modifications of the respective embodiments) explained above, light near the wavelength of 540 nm is used as the third narrowband light NL3 in order to display the capillaries in the surface layer of the living body tissue. However, wavelength of the third narrowband light NL3 is not limited to the light. For example, as the wavelength of the third narrowband light NL3, light near a wavelength of 415 nm or light near a wavelength of 460 nm shorter than the wavelength of 540 nm may be used. In particular, in order to obtain information concerning the surface layer of the living tissue, the light near the wavelength of 415 nm or the light near the wavelength of 460 nm shorter than the light near the wavelength of 540 nm is desirable.

(Modification 4)

In the light source devices in the respective embodiments and the respective modifications (including the modifications of the respective embodiments) explained above, it is explained that the lamp of the heat light source, the LED, the LD, or the like is used. However, other means may be used. For example, as the light source means for the light source section, a variable wavelength laser may be used or a phosphor may be excited by the LED or the LD to generate broadband light and use the light.

(Modification 5)

In the endoscope apparatuses in the respective embodiments and the respective modifications (including the modifications of the respective embodiments) explained above, when narrowband light is irradiated, for example, the narrowband light near the wavelength of 600 nm may be generated by a laser and the narrowband light near the wavelength of 630 nm may be generated by the LED. The narrowband light near the wavelength 600 nm may be generated by the LED and the narrowband light near the wavelength of 630 nm may be generated by the laser. When the laser is used, it is possible to reduce noise in a depth direction.

(Modification 6)

Figure 31:
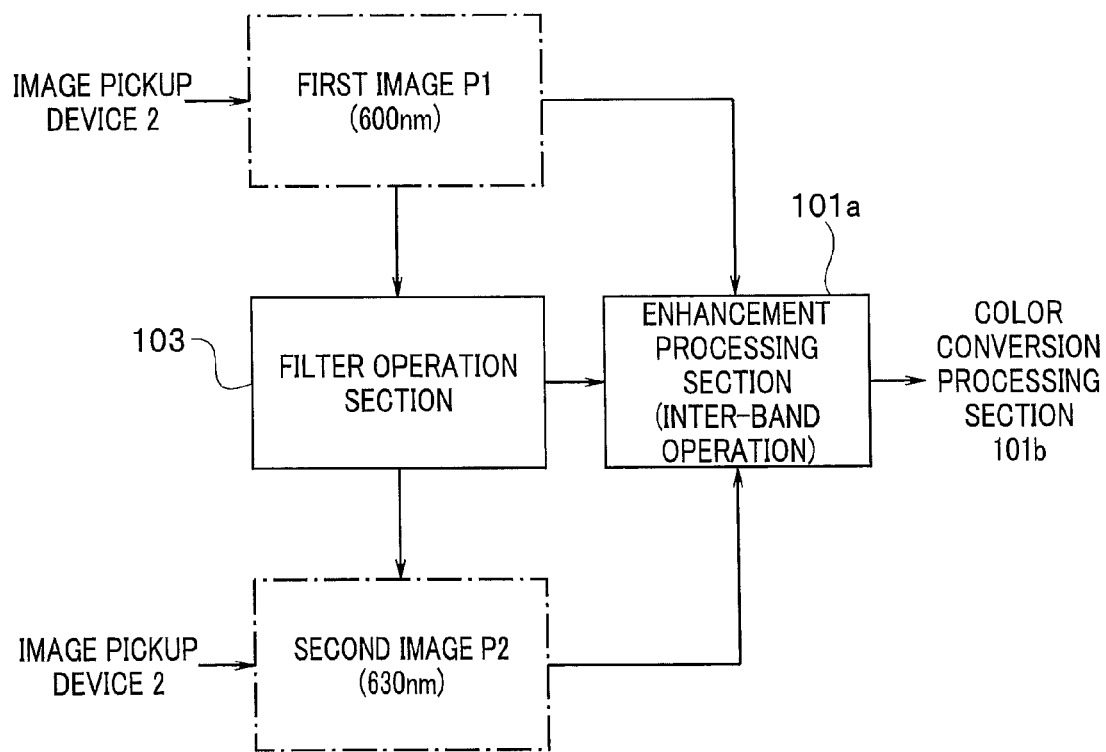
FIG. 31 is a diagram for explaining a configuration of a processing section configured to generate, from one of two narrowband lights, the other of the two narrowband lights according to a modification 6 common to the respective embodiments.
Figure 32:
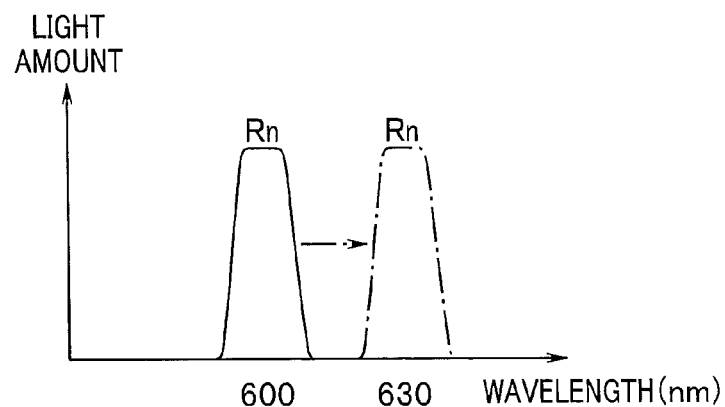
FIG. 32 is a diagram showing a spectral characteristic for explaining narrowband light generated in a pseudo manner according to the modification 6 common to the respective embodiments.

In the respective embodiments and the respective modifications (including the modifications of the respective embodiments) explained above, the enhancement processing is performed for the two narrowband lights. However, one of the two narrowband lights to be subjected to the enhancement processing may be generated in a pseudo manner. FIG. 31 is a diagram for explaining a configuration of a processing section configured to generate, from one of two narrowband lights, the other of the two narrowband lights. FIG. 32 is a diagram showing a spectral characteristic for explaining narrowband light generated in a pseudo manner.

The first image signal P1 of the return light of the narrowband light near the wavelength of 600 nm is inputted to a filter operation section 103. The filter operation section 103 applies, to the inputted first image signal P1, for example, filtering for reducing a difference in light and shade as a whole and making an edge portion less conspicuous and outputs the second image signal P2 as a pseudo image. The enhancement processing section 101*a* applies the enhancement processing to the first image signal P1 and the second image signal P2, which is the pseudo image.

According to such processing, from one image to be subjected to the enhancement processing, a pseudo image of the other may be generated to perform the enhancement processing.

Note that, in FIG. 32, a pseudo image corresponding to the narrowband light near the wavelength of 630 nm is generated from the first image signal P1 of the return light of the narrowband light near the wavelength of 600 nm. However, a pseudo image corresponding to the narrowband light near the wavelength of 600 nm may be generated from the first image signal P1 of the return light of the narrowband light near the wavelength of 630 nm and the third image signal P3 of the return light of the narrowband light near the wavelength of 540 nm.

Furthermore, in FIG. 32, the pseudo image is generated with respect to an image of return light of real illumination light. However, a pseudo image obtained by generating one spectrally estimated image in the second or third embodiment from the other spectrally estimated image with the filter operation section 103 may be used. The enhancement processing is performed between the spectrally estimated image, which is one pseudo image and the other spectrally estimated image or the real image.

As explained above, the enhancement processing may be performed using the pseudo image.
(Modification 7)

In the respective embodiments and the respective modifications (including the modifications of the respective embodiments) explained above, one enhancement processing result is obtained with respect to images of two narrowband lights. However, two or more enhancement processing results may be further obtained.

Figure 33:
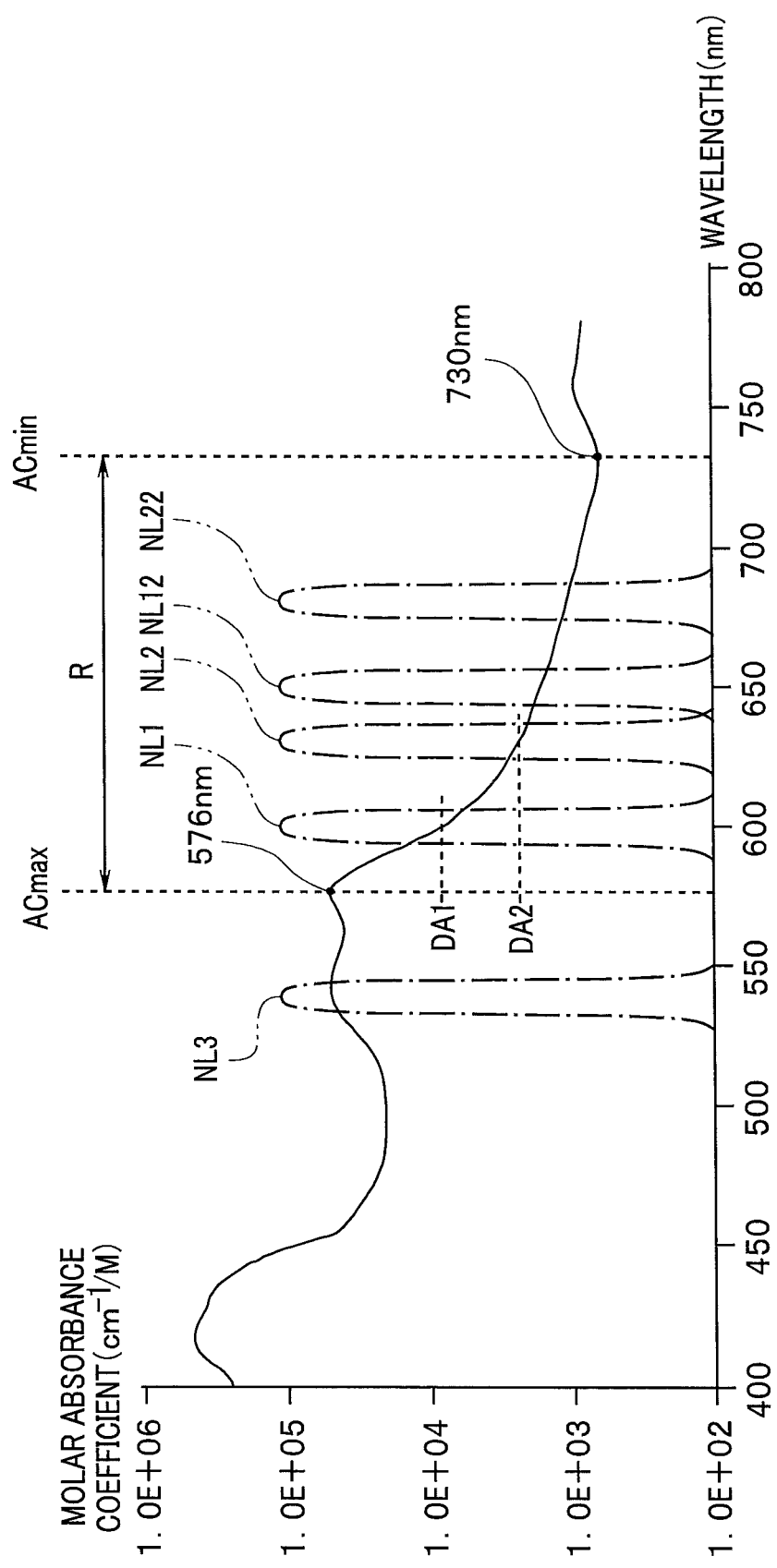
FIG. 33 is a diagram showing a light absorption characteristic of venous blood for explaining a modification 7 common to the respective embodiments.

FIG. 33 is a diagram showing a light observation characteristic of venous blood for explaining the modification 7. In FIG. 33, to obtain two enhancement processing results, for one enhancement processing result, the enhancement processing is applied to a first combination of the narrowband light NL1 near the wavelength of 600 nm and the narrowband light NL2 near the wavelength of 630 nm and, for the other enhancement processing result, the enhancement processing is applied to a second combination of narrowband light NL12 near the wavelength of 650 nm and narrowband light NL22 near the wavelength of 680 nm. A user is allowed to select any one of the combinations. For example, the user can select, according to mode selection, in which of the combinations display is performed.

Note that another combination may be a combination such as a combination of the narrowband light near the wavelength of 615 nm and the narrowband light near the wavelength of 645 nm or a combination of the narrowband light near the wavelength of 630 nm and the narrowband light near the wavelength of 660 nm.

In the case of the second combination, since wavelength in use is shifted to the long wavelength side compared with the first combination, an image in a deeper part is enhanced. Therefore, when the surgeon desires to enhance a blood vessel in a deeper part, if blood, bile, urine, or the like adheres to a mucosal surface of a living body, it is possible to highlight a desired blood vessel by selecting the second combination.

The enhancement processing for two or more combinations can be performed by increasing combinations of rotating filters in the light source device or increasing the number of spectrally estimated image signals to be estimated by the spectral estimation processing.

When a blood vessel relatively shallow from the mucosal surface is highlighted and displayed, combinations of wavelengths of narrowband lights preferably include two combinations, i.e., a combination of wavelength near the wavelength of 580 nm and wavelength near the wavelength of 630 nm and a combination of wavelength near the wavelength of 590 nm and wavelength near the wavelength of 630 nm.

When a blood vessel in a deeper part from the mucosal surface or a blood vessel under a mucosa under blood or the like is highlighted, combinations of wavelengths of narrowband lights preferably include two combinations, i.e., a combination of wavelength near the wavelength of 600 nm and wavelength near the wavelength of 630 nm and a combination of wavelength near the wavelength of 650 nm and wavelength near the wavelength of 680 nm.

In the example explained above, the combinations are the two combinations. However, the combinations may be three combinations. In the case of the three combinations, the combinations include, for example, a first combination of the narrowband light near the wavelength of 600 nm and the narrowband light near the wavelength of 630 nm, a second combination of the narrowband light near the wavelength of 650 nm and the narrowband light near the wavelength of 680 nm, and a third combination of the narrowband light near the wavelength of 700 nm and the narrowband light near the wavelength of 730 nm.

As explained above, a plurality of enhancement processing results are obtained. Therefore, if concentration of blood or the like adhering to a mucosal surface of a living body is high, the surgeon selects a combination on a longer wavelength side (e.g., the combination of the wavelength near the wavelength of 650 nm and the wavelength near the wavelength of 680 nm). When a blood vessel is present in a relatively shallow part, if concentration of blood or the like adhering to the mucosal surface of the living body is low, the surgeon selects a combination on a shorter wavelength side (e.g., the combination of the wavelength near the wavelength of 580 nm and the wavelength near the wavelength of 630 nm). Consequently, the user can highlight a desired blood vessel.
(Modification 8)

In the respective embodiments and the respective modifications (including the modifications of the respective embodiments) explained above, a wavelength difference between two narrowband lights for the enhancement processing is fixed. However, one narrowband light may be fixed and the other may be variable.

For example, in the case of the narrowband light near the wavelength of 600 nm and the narrowband light near the wavelength of 630 nm, the narrowband light near the wavelength of 600 nm may be fixed and the other narrowband light may be able to be arbitrarily set to be variable from the narrowband light near the wavelength of 630 nm to the narrowband light near the wavelength of 730 nm. Alternatively, the other narrowband light near the wavelength of 730 nm may be fixed and the other narrowband light may be able to be arbitrarily set to be variable from the narrowband light near the wavelength of 590 nm to the narrowband light near the wavelength of 620 nm. Note that the narrowband light near 600 nm may be fixed and the other narrowband light may be able to be arbitrarily set to wavelength band equal to or higher than 730 nm.

In this way, one of the two narrowband lights is fixed and the other is set variable. Consequently, it is possible to further highlight a blood vessel in a desired region.
(Modification 9)

In the respective embodiments and the respective modifications (including the modifications of the respective embodiments) explained above, three images are obtained and a narrowband image is displayed on the observation monitor 5. However, a fourth image may be obtained and a display image may be selected out of the four images as appropriate and generated.

The endoscope apparatus has the narrowband light observation mode in addition to the normal light observation mode.

The surgeon switches the normal light observation mode to the narrowband light observation mode when necessary and performs various kinds of treatment. By adding the fourth image, it is possible to easily obtain display images in the respective observation modes.

For example, the fourth image is obtained by using a light source device that can further irradiate illumination light of blue narrowband light (or may be wideband light) having a wavelength shorter than the wavelength of 540 nm. The light source device alternately irradiates, on an object, illumination light of a first combination of the light having a fourth wavelength and the narrowband light near the wavelength of 600 nm and illumination light of a second combination of the narrowband light near the wavelength of 540 nm and the narrowband light near the wavelength of 630 nm Note that the light source device may alternately irradiate, on the object, illumination light of a combination of the light having the fourth wavelength, the narrowband light near the wavelength of 540 nm, and the narrowband light near the wavelength of 600 nm and illumination light of the narrowband light near the wavelength of 630 nm.

Return lights of the respective illumination lights are received by an image pickup device including an RGB color filter. For example, an image of the return light having the fourth wavelength is picked up in a B band of the color filter and an image of the return light of the narrowband light near the wavelength of 600 nm is picked up in an R band. The color filter of the image pickup device may be a color filter of the complementary color system. Furthermore, the image pickup device may be a monochrome image pickup device.

Since the images of the respective bands are separated, four monochrome images are obtained in the video processor 7. Note that, in order to obtain the respective images, appropriate color balance adjustment is applied to image signals of the respective lights.

In the video processor 7, a normal image for the normal light observation mode is generated using images of four return lights of the light having the fourth wavelength, the narrowband light near the wavelength of 540 nm, the narrowband light near the wavelength of 600 nm, and the narrowband light near the wavelength of 630 nm.

In the video processor 7, a first narrowband light image is generated by allocating an image signal of the light having the fourth wavelength to the B and G channels and allocating an image signal of the narrowband light near the wavelength of 540 nm to the R channel and using two images of the light having the fourth wavelength and the narrowband light near the wavelength of 540 nm.

Further, in the video processor 7, a second narrowband light image is generated using three images of the narrowband light near the wavelength of 540 nm, the narrowband light near the wavelength of 600 nm, and the narrowband light near the wavelength of 630 nm.

Note that an image signal of the narrowband light near the wavelength of 600 nm is subjected to the enhancement processing.

According to an image display instruction by the surgeon, the images generated as explained above are selected and displayed on the observation monitor 5.

With such a configuration, it is also possible to perform simultaneous display of a normal image for normal light observation and a narrowband light image for narrowband light observation or superimposed display of the normal image and the narrowband light image. For example, it is possible to perform parallel display of a normal light image and the first narrowband light image (or the second narrowband light image) or parallel display of the first narrowband light image and the second narrowband light image.

Further, it is possible to generate a superimposed image obtained by adding blood vessel information of a deep part to the normal image and display the superimposed image on the observation monitor by allocating an image signal of the light having the fourth wavelength to the B channel, allocating an image signal of the narrowband light near the wavelength of 540 nm to the G channel, and allocating an image signal of the narrowband light near the wavelength of 600 nm to the R channel or allocating the image signal of the light having the fourth wavelength to the B channel, allocating the image signal of the narrowband light near the wavelength of 540 nm and the image signal of the narrowband light near the wavelength of 600 nm to the G channel, and allocating the image signal of the narrowband light near the wavelength of 600 nm (or the image signal of the narrowband light near the wavelength of 600 nm and the image signal of the narrowband light near the wavelength of 630 nm) to the R channel.

Furthermore, it is possible to generate an image in which both of a blood vessel in a surface layer and a blood vessel in a deep part are emphasized and display the image on the observation monitor 5 by allocating the image signal of the light having the fourth wavelength to the B channel, allocating the image signal of the light having the fourth wavelength and the image signal of the narrowband light near the wavelength of 600 nm to the G channel, and allocating the image signal of the narrowband light near the wavelength of 600 nm (or the image signal of the narrowband light near the wavelength of 600 nm and the image signal of the narrowband light near the wavelength of 630 nm) to the R channel.

Note that the image signal of the fourth wavelength may be generated according to the spectral estimation.

As explained above, according to the modification 9, it is possible to perform parallel display or superimposed display of the normal image and the narrowband light image.

As explained above, according to the respective embodiments and the respective modifications (including the modifications of the respective embodiments) explained above, it is possible to provide an endoscope apparatus that can clearly display a blood vessel in a mucosa deep part without performing complicated work of drug administration.

The present invention is not limited to the embodiments explained above. Various changes, alterations, and the like are possible in a range in which the gist of the present invention is not changed.

What is claimed is:

1. An endoscope apparatus comprising:
   an illumination section configured to irradiate at least one or more illumination lights having a predetermined wavelength band on a subject;
   an image pickup section configured to pick up an image of return light from the subject based on the irradiation by the illumination section; and
   an image processing section configured to enhance a blood vessel at a predetermined depth in an observation image, the image processing section implementing the functions of:
   based on luminance values of two image pickup signals, the two image pickup signals being an image pickup signal corresponding to a first wavelength band having a spectral characteristic of a narrowband and an image pickup signal corresponding to a second wavelength band having a spectral characteristic of a narrowband in which an absorption coefficient in the hemoglobin absorption characteristic is lower than an absorption coefficient of the signal corresponding to the first wavelength band and a scattering characteristic of the living tissue is suppressed more than the scattering characteristic of the signal corresponding to the first wavelength band between a wavelength including a maximum value and a wavelength including a minimum value on a hemoglobin light absorption characteristic of a living tissue of the subject, calculating a change amount of luminance value between the two image pickup signals which represents a distribution with 0 set as a reference;

multiplying the calculated change amount of luminance value between the two image pickup signals which represents a distribution with 0 set as a reference by an enhancement coefficient for enhancing the blood vessel at the predetermined depth; and causing the change amount of luminance value multiplied by the enhancement coefficient to be reflected on the image pickup signal corresponding to the first wavelength band.

2. The endoscope apparatus according to claim 1, wherein the illumination section irradiates, a first illumination light having a first wavelength band and a second illumination light having the second wavelength band in a red band of a visible range.

3. The endoscope apparatus according to claim 2, wherein the endoscope apparatus has a normal light observation mode and a narrowband light observation mode, and the illumination section irradiates the first illumination light and the second illumination light in the narrowband light observation mode.

4. The endoscope apparatus according to claim 3, wherein the illumination section includes a filter for the normal light observation mode and a filter for the narrowband light observation mode for transmitting light from a light source, and the illumination section irradiates the first illumination light and the second illumination light by emitting the light from the light source through the filter for the narrowband light observation mode in the narrowband light observation mode.

5. The endoscope apparatus according to claim 1, further comprising a spectral estimation section configured to generate and output at least two spectrally estimated image signals as the image pickup signal corresponding to the first wavelength band and the image pickup signal corresponding to the second wavelength band according to spectral estimation processing on the basis of at least two image pickup signals of the return light from the subject.

6. The endoscope apparatus according to claim 5, wherein the illumination section irradiates two or more illumination lights, and a wavelength band of at least one illumination light of the two or more illumination lights is narrower than a wavelength band of the other illumination lights.

7. The endoscope apparatus according to claim 2, wherein the first illumination light is narrowband light having a wavelength of 585 nm to 615 nm, and the second illumination light is narrowband light having a wavelength of 610 nm to 730 nm.

8. The endoscope apparatus according to claim 2, wherein the first illumination light is narrowband light near a wavelength of 600 nm, and the second illumination light is narrowband light near a wavelength of 630 nm.

9. The endoscope apparatus according to claim 2, wherein the first illumination light is narrowband light near a wavelength of 600 nm, and the second illumination light is narrowband light having a peak wavelength in a wavelength band of a wavelength equal to or longer than 730 nm.

10. The endoscope apparatus according to claim 1, wherein the image processing section calculates a result of division obtained by division of the luminance values of the two image pickup signals, and calculates a change amount of luminance value between the two image pickup signals by causing the result of division to be a distribution with 0 set as a reference.

11. The endoscope apparatus according to claim 10, wherein the image processing section subtracts a predetermined numerical value from the result of division, to thereby calculate a change amount of luminance value between the two image pickup signals which represents a distribution with 0 set as a reference.

12. The endoscope apparatus according to claim 11, wherein the image processing section:

divides the image pickup signal corresponding to the first wavelength band by the image pickup signal corresponding to the second wavelength band to calculate the result of division, and further generates a first averaging signal obtained by averaging the image pickup signal corresponding to the first wavelength band by pixels, generates a second averaging signal obtained by averaging the image pickup signal corresponding to the second wavelength band by pixels, and divides the second averaging signal by the first averaging signal, to calculate the predetermined numerical value.

13. The endoscope apparatus according to claim 1, wherein, in the image processing section, the first wavelength band and the second wavelength band are in a visible red band.

* * * * *